United States Patent
Sarnaik et al.

(10) Patent No.: US 12,291,724 B2
(45) Date of Patent: *May 6, 2025

(54) TUMOR-INFILTRATING LYMPHOCYTES FOR ADOPTIVE CELL THERAPY

(71) Applicants: H. LEE MOFFITT CANCER CENTER AND RESEARCH INSTITUTE, INC., Tampa, FL (US); UNIVERSITY OF SOUTH FLORIDA, Tampa, FL (US)

(72) Inventors: Amod A. Sarnaik, Tampa, FL (US); Shari Pilon-Thomas, Tampa, FL (US); Mark McLaughlin, Tampa, FL (US); Hao Liu, Tampa, FL (US)

(73) Assignees: H. LEE MOFFITT CANCER CENTER AND RESEARCH INSTITUTE, INC., Tampa, FL (US); UNIVERSITY OF SOUTH FLORIDA, Tampa, FL (US)

(*) Notice: Subject to any disclaimer, the term of this patent is extended or adjusted under 35 U.S.C. 154(b) by 139 days.

This patent is subject to a terminal disclaimer.

(21) Appl. No.: 17/752,481

(22) Filed: May 24, 2022

(65) Prior Publication Data

US 2022/0282215 A1    Sep. 8, 2022

Related U.S. Application Data

(63) Continuation of application No. 16/272,524, filed on Feb. 11, 2019, now Pat. No. 11,518,980, which is a continuation of application No. 15/126,436, filed as application No. PCT/US2015/021759 on Mar. 20, 2015, now abandoned.

(60) Provisional application No. 61/973,002, filed on Mar. 31, 2014, provisional application No. 61/955,970, filed on Mar. 20, 2014.

(51) Int. Cl.
| | | |
|---|---|---|
| C12N 5/0783 | (2010.01) | |
| A61K 35/12 | (2015.01) | |
| A61K 39/00 | (2006.01) | |
| G01N 33/50 | (2006.01) | |

(52) U.S. Cl.
CPC .......... *C12N 5/0636* (2013.01); *A61K 35/12* (2013.01); *A61K 39/4611* (2023.05); *A61K 39/46449* (2023.05); *G01N 33/505* (2013.01); *A61K 2239/57* (2023.05); *C12N 2501/05* (2013.01); *C12N 2501/056* (2013.01); *C12N 2501/2302* (2013.01); *C12N 2501/50* (2013.01); *C12N 2501/998* (2013.01); *C12N 2501/999* (2013.01)

(58) Field of Classification Search
None
See application file for complete search history.

(56) References Cited

U.S. PATENT DOCUMENTS

| | | | |
|---|---|---|---|
| 5,579,250 A | 11/1996 | Balaji et al. | |
| 5,612,895 A | 3/1997 | Balaji et al. | |
| 5,631,280 A | 5/1997 | Ciccarone et al. | |
| 5,811,515 A | 9/1998 | Grubbs et al. | |
| 7,192,713 B1 | 3/2007 | Verdine et al. | |
| 7,723,469 B2 | 5/2010 | Walensky et al. | |
| 7,786,072 B2 | 8/2010 | Verdine et al. | |
| 8,198,405 B2 | 6/2012 | Walensky et al. | |
| 8,324,428 B2 | 12/2012 | Verdine et al. | |
| 8,592,377 B2 | 11/2013 | Verdine et al. | |
| 2010/0189728 A1 | 7/2010 | Schendel et al. | |
| 2011/0052530 A1 | 3/2011 | Dudley et al. | |
| 2011/0091967 A1 | 4/2011 | Valmori et al. | |
| 2017/0081635 A1 | 3/2017 | Sarnaik et al. | |

FOREIGN PATENT DOCUMENTS

| | | |
|---|---|---|
| CN | 101351546 A | 1/2009 |
| CN | 103243072 A | 8/2013 |
| CN | 103396992 A | 11/2013 |
| CN | 103520198 B | 1/2016 |
| JP | H10-507627 A | 7/1998 |
| JP | 2017511375 A | 4/2017 |
| WO | 199606929 A2 | 3/1996 |
| WO | 2009/062001 A1 | 5/2009 |
| WO | 2011053223 A1 | 5/2011 |
| WO | 2012127464 A1 | 9/2012 |
| WO | 2013192628 A1 | 12/2013 |

OTHER PUBLICATIONS

Communication pursuant to Article 94(3) EPC issued for European Application No. dated Oct. 17, 2022.
Translation of Office Action issued for Eurasian Application No. 201892645, dated Oct. 19, 2022.
Wu R, Forget MA, Chacon J, Bernatchez C, Haymaker C, Chen JQ, Hwu P, Radvanyi LG. Adoptive T-cell therapy using autologous tumor-infiltrating lymphocytes for metastatic melanoma: current status and future outlook. Cancer J. Mar.-Apr. 2012; 18(2): 160-75. doi: 10.1097/PPO.0b013e31824d4465.PMID: 22453018; PMCID: PMC3315690.
Translation of Office Action issued for Korean Application No. 10-2016-7029042, dated Nov. 4, 2022.
Office Action issued for Japanese Application No. 2020-121328, dated Jan. 10, 2023.

(Continued)

*Primary Examiner* — Daniel C Gamett
(74) *Attorney, Agent, or Firm* — Meunier Carlin & Curfman LLC

(57) ABSTRACT

Disclosed are compositions and methods for ex vivo expansion of tumor infiltrating lymphocytes for use in adoptive cell therapy (ACT). Also disclosed are compositions and method for identifying an agent for ex vivo expansion of tumor infiltrating lymphocytes for use in ACT. Also disclosed are methods for treating cancer using tumor-infiltrating lymphocytes expanded by the disclosed methods.

25 Claims, 14 Drawing Sheets

(56) References Cited

OTHER PUBLICATIONS

Klapper, Jacob A., et al. "Single-pass, closed-system rapid expansion of lymphocyte cultures for adoptive cell therapy." Journal of immunological methods 345.1-2 (2009): 90-99.
Somerville, Robert, et al. "Clinical scale rapid expansion of lymphocytes for adoptive cell transfer therapy in the WAVE® bioreactor." Journal of translational medicine 10.1 (2012): 1-11.
Examination report No. 2 issued for Australian Application No. 2020256412, dated Jan. 18, 2023.
International Search Report and Written Opinion issued in International Application No. PCT/US2015/021759, mailed Jun. 24, 2015.
Dudley, et al., "Adoptive Cell Transfer Therapy Following Non-Myeloablative but Lymphodepleting Chemotherapy for the Treatment of Patients with Refractory Metastatic Melanoma", Journal of Clinical Oncology, 2005, vol. 23, No. 10, pp. 2346-2357.
Pilon-Thomas S, et al. "Brief Communication: Efficacy of Adoptive Cell Transfer of Tumor Infiltrating Lymphocytes after Lymphopenia Induction for Metastatic Melanoma", J Immunother. 2012 35(8):615-20.
Rosenberg SA, et al. "Durable Complete Responses in Heavily Pretreated Patients with Metastatic Melanoma Using T Cell Transfer Immunotherapy", Clinical cancer research: an official journal of the American Association for Cancer Research. 2011 17(13):4550-7.
Xiao, et al., "Local administration of TLR ligands rescues the function of tumor-infiltrating CD8 T cells and enhances the antitumor effect of lentivector immunization" J Immunol. 2013, 190(11): 5866-5873.
Xu, et al., "CpG Oligodeoxynucleotides Enhance the Efficacy of Adoptive Cell Transfer Using Tumor Infiltrating Lymphocytes by Modifying the Th1 Polarization and Local Infiltration of Th17 Cells", Clin Dev Immunol. 2010, 410893.
Extended European Search Report issued for Application No. 15765854, dated Feb. 5, 2018, 10 pages.
Chacon, et al., "Manipulating the Tumor Microenviroment Ex Vivo for Enhanced Expansion of Tumor-Infiltrating Lymphoocytes for Adaptive Cell Therapy" Clinical Cancer Research 21(3), 2015, 611-621.
Chacon, et al., "Co-stimulation through 4-1BB/CD137 improves the expansion and function of CD8(+) melanoma tumor-infiltrating lymphocytes for adoptive T-cell therapy." PLoS One. 2013;8(4):e60031.
Paulos, et al., "Toll-like Receptors in Tumor Immunotherapy", Clinical Cancer Research, 2007, vol. 13, Issue 18, pp. 5280-5289.
Andreani, et al. "Activation of Toll-like receptor 4 on tumor cells in vitro inhibits subsequent tumor growth in vivo." Cancer research 67.21 (2007): 10519-10527.
Scarlett, Uciane K., et al. "In situ stimulation of CD40 and toll-like receptor 3 transforms ovarian cancer—infiltrating dendritic cells from immunosuppressive to immunostimulatory cells." Cancer research 69.18 (2009): 7329-7337.
Communication Pursuan to Rule 164(1) EPC, issued for Application No. 15765854, dated Oct. 27, 2017, 11 pages.
Examination report No. 1 issued for Australian Application No. 2015231041, dated May 30, 2019.
Office Action issued for Japanese Application No. 2017-501131, dated Apr. 2, 2019.
Search Report issued for Chinese Application No. 2015800226903, dated Feb. 2, 2019.
Supplementary Search Report issued for Chinese Application No. 2015800226903, dated Oct. 18, 2019.
International Preliminary Report on Patentability issued in International Application No. PCT/US2015/021759, mailed Sep. 29, 2016.
Office Action issued for Chinese Application No. 201580022690.3, dated May 14, 2020.
Office Action issued for Japanese Application No. 2017-501131, dated Mar. 17, 2020.
Extended European Search Report issued for Application No. 19220121.8, dated Jun. 9, 2020.
Peng, Guangyong, et al. "Tumor-infiltrating γδ T cells suppress T and dendritic cell function via mechanisms controlled by a unique toll-like receptor signaling pathway." Immunity 27.2 (2007): 334-348.
Salem, Mohamed Labib. "Triggering of toll-like receptor signaling pathways in T cells contributes to the anti-tumor efficacy of T cell responses." Immunology letters 137.1-2 (2011): 9-14.
Salem, Mohamed L., et al. "The TLR3 agonist poly (I: C) targets CD8+ T cells and augments their antigen-specific responses upon their adoptive transfer into naive recipient mice." Vaccine 27.4 (2009): 549-557.
Gorter, A., et al. "Enhancement of the lytic activity of cloned human CD8 tumour-infiltrating lymphocytes by bispecific monoclonal antibodies." Clinical & Experimental Immunology 87.1 (1992): 111-116.
Kaczanowska, Sabina, Ann Mary Joseph, and Eduardo Davila. "TLR agonists: our best frenemy in cancer Immunotherapy." Journal of leukocyte biology 93.6 (2013): 847-863.
Duthie, Malcolm S., et al. "Use of defined TLR ligands as adjuvants within human vaccines." Immunological reviews 239.1 (2011): 178-196.
Saint-Jean, M., et al. "P003. TLR7 and TLR8 expression by melanoma cells correlates with a better relapse-free survival for stage III melanoma patients." Melanoma Research 21 (2011): e18.
Rong-Fu, Wang, "Regulatory T cells in Tumor Immunity: Role of Toll-Like Receptors", Cancer Immunity, 2007, Ch 15., 277-287.
Knol, Anne Chantal, et al. "Absence of amplification of CD4+ CD25high regulatory T cells during in vitro expansion of tumor-infiltrating lymphocytes in melanoma patients." Experimental dermatology 17.5 (2008): 436-445.
Official Action for the Korean Patent Application No. 10-2016-7029042, dated Aug. 3, 2021.
Official Action for the Eurasian Patent Application No. 201892645/28, dated Aug. 9, 2021.
Official Action for the Japanese Patent Application No. 2020-121328, dated Aug. 17, 2021.
Oliver M. et al. TLR Ligands in the Local Treatment of Established Intracerebral Murine Gliomas. The Journal of Immunology. Nov. 15, 2008, 181 (10), 6720-6729.
Oberg, Hans-Heinrich et al. "Regulation of T cell activation by TLR ligands". European journal of cell biology, vol. 90,6-7 (2011): 582-92.
Zuliani, et al., Value of large scale expansion of tumor infiltrating lymphocytes in a compartmentalised gas-permeable pag: interests for adoptive immunotherapy. Journal of Translational Medicine 2011, 9:63.
Japanese Office Action issued for Application No. 2020-121328, dated May 24, 2022.
Eurasian Office Action issued for Application No. 201892645, dated Mar. 16, 2022.
Korean Office Action issued for Application No. 10-2016-7029042, dated Jun. 17, 2022.
Paijens ST. et al., Cell Mol Immunol, 2021 year, vol. 18,pp. 842-859. 18 pages.
Herberhold S. et al., Antivir Ther, 2011 year, vol. 16, pp. 751-758. 8 pages.
Office Action issued for Korean Application No. 10-2016-7029042, dated Mar. 6, 2023. 6 pages.
Office Action issued for Mexican Application No. MX/a/2020/005634, dated Aug. 2, 2024. 4 pages.
Office Action issued for Japanese Application No. 2023-113229, dated Dec. 12, 2023. 12 pages.
Office Action issued for Japanese Application No. 2023-113229, dated Aug. 20, 2023. 9 pages.
Office Action and Search Report issue for Chinese Application No. 010-88091921, dated Mar. 23, 2023. 11 pages.
Notice of Allowance issued for Canadian Application No. 2,943,389, dated May 29, 2023. 1 page.
Communication Pursuant to Article 94(3) EPC issued for European Application No. 19 220 121.8, dated Aug. 9, 2022. 3 pages.
Office Action issued for Korean Application No. 2023-113229, dated Jul. 3, 2024. 7 pages.
First Examination Report issued for New Zealand Application No. 762786, dated May 10, 2023. 3 pages.

(56) References Cited

OTHER PUBLICATIONS

Second Examination Report issued for New Zealand Application No. 762786, dated Sep. 4, 2023. 3 pages.
Third Examination Report issued for New Zealand Application No. 762786, dated Jan. 24, 2024. 3 pages.
Fourth Examination Report issued for New Zealand Application No. 762786, dated Apr. 26, 2024. 4 pages.
Office Action issued for Korean Application No. 2023-70188859, dated Oct. 20, 2023. 6 pages.
Office Action issued for Eurasian Application No. 201892645, dated Jul. 10, 2024. 4 pages.
First Examination Report issued for New Zealand Application No. 744131, dated Apr. 12, 2023. 3 pages.

TUMOR-INFILTRATING LYMPHOCYTES FOR ADOPTIVE CELL THERAPY

CROSS-REFERENCE TO RELATED APPLICATIONS

This application claims benefit of U.S. application Ser. No. 16/272,524, filed Feb. 11, 2019, which is a continuation of U.S. application Ser. No. 15/126,436, filed Sep. 15, 2016, which is a 371 National Stage Application of PCT/US2015/021759, filed Mar. 20, 2015, which claims priority to U.S. Provisional Application No. 61/955,970, filed Mar. 20, 2014, and U.S. Provisional Application No. 61/973,002, filed Mar. 31, 2014, all of which are hereby incorporated herein by reference in their entirety.

BACKGROUND

Adoptive cell therapy (ACT) with tumor-infiltrating lymphocytes (TIL) is a promising form of T cell-based immunotherapy. Preparation of TIL involves surgical resection and expansion of TIL from melanoma tumors. Upon adequate TIL expansion, patients undergo lymphodepleting chemotherapy, and TIL adoptive transfer followed by high dose IL-2. The Surgery Branch at the National Cancer Institute has pioneered this treatment for metastatic melanoma and reported an approximately 50% response rate in treated patients, with ~20% of patients achieving durable complete responses (Rosenberg S A, et al. Clinical cancer research: an official journal of the American Association for Cancer Research. 2011 17(13):4550-7). The impressive durability of responses to ACT is a hallmark of this treatment and appears to be superior to existing treatments for melanoma. ACT depends upon infiltration of T cells into tumors prior to harvest, successful ex vivo expansion of TIL, and potent anti-tumor effector function after transfer. Although TIL ACT is effective for melanoma, durable response rates need further improvement. Shortening the expansion period for initial TIL growth and improving the tumor-specificity of expanded TILs may increase response rates in patients treated with autologous TIL.

SUMMARY

Disclosed are compositions and methods for ex vivo expansion of tumor-infiltrating lymphocytes for use in adoptive cell therapy (ACT). In some, embodiments, the methods involve culturing the lymphocytes to produce expanded lymphocytes in a culture medium comprising a toll like receptor (TLR) agonist in an amount effective to improve the tumor-specificity of the expanded lymphocytes. In some embodiments, the methods involve culturing the lymphocytes to produce expanded lymphocytes in a culture medium comprising a stimulatory peptide or peptidomimetic. In some embodiments, the peptidomimetic is a peptoid or peptide-peptoid hybrid. In some embodiments, the peptoid or peptide-peptoid hybrid is stabilized by a hydrocarbon staple.

Also disclosed are methods for treating cancer using tumor-infiltrating lymphocytes expanded by the disclosed methods. In some embodiments, the methods involve obtaining autologous tumor-infiltrating lymphocytes from the subject, culturing the lymphocytes in a culture medium comprising a toll like receptor (TLR) agonist to produce expanded lymphocytes, treating the subject with nonmyeloablative lymphodepleting chemotherapy, and administering the expanded lymphocytes to the mammal.

In some embodiments, the cancer is a solid tumor. In some cases, the cancer is a melanoma, ovarian cancer, breast cancer, and colorectal cancer. The cancer can be metastatic, recurrent, or a combination thereof.

The TLR agonist is in some embodiments a ligand for a TLR selected from the group consisting of TLR1, TLR2, TLR3, TLR4, and TLR9. For example, the TLR agonist can be a ligand selected from the group consisting of Pam3CSK4, Pam3CSK4, poly I:C, Ribomunyl, and CpG ODN.

Also disclosed are compositions and method for identifying an agent for ex vivo expansion of tumor-infiltrating lymphocytes for use in ACT. The methods can involve contacting tumor-infiltrating lymphocytes with a candidate peptide or peptidomimetic from a peptide or peptidomimetic library for the ability to selectively bind the tumor-infiltrating lymphocytes. In some embodiments, the peptidomimetic is a peptoid or peptide-peptoid hybrid. In some embodiments, the peptoid or peptide-peptoid hybrid is stabilized by a hydrocarbon staple. The method can further involve screening the effect of a binding peptide or peptidomimetic on the proliferation of the tumor-infiltrating lymphocytes. In some embodiments, identification of a candidate peptide or peptidomimetic that increases proliferation of the tumor-infiltrating lymphocytes identifies an agent for ex vivo expansion of tumor-infiltrating lymphocytes for use in ACT. Agents identified by these methods can be used to expand tumor-infiltrating lymphocytes for use in ACT.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
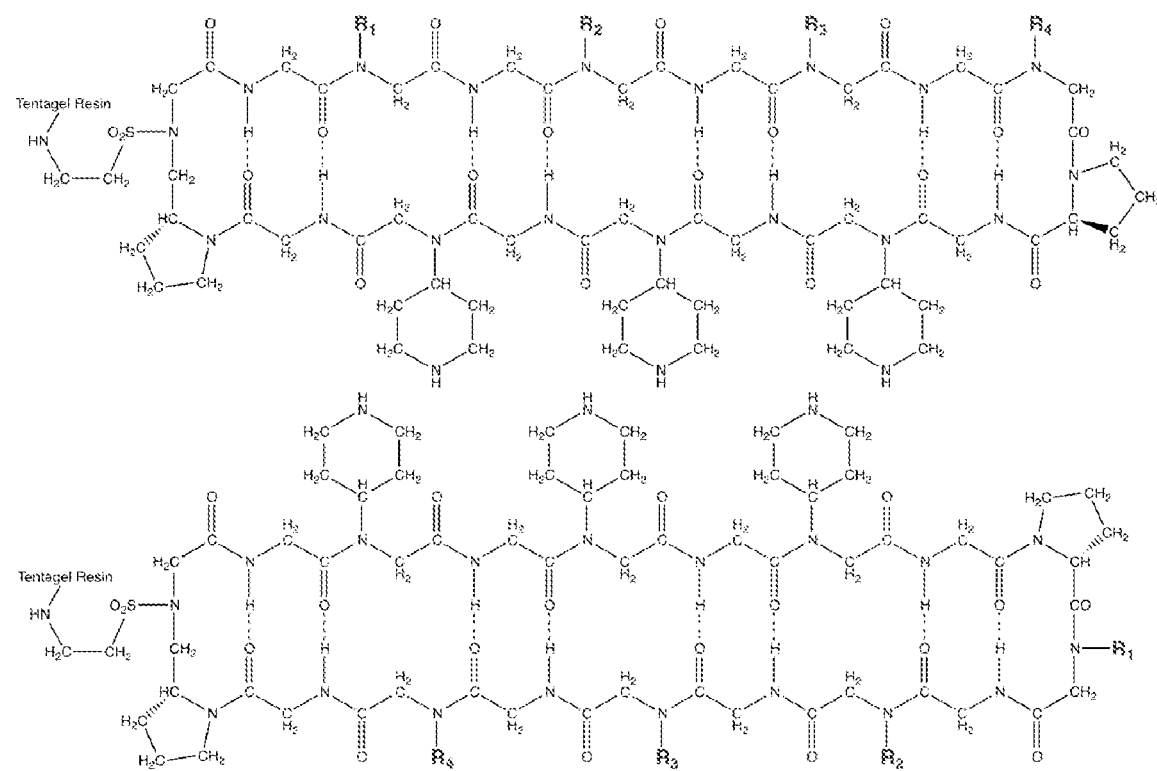
FIGS. 1A to 1D show examples of peptoid-bodies.
Figure 1B:
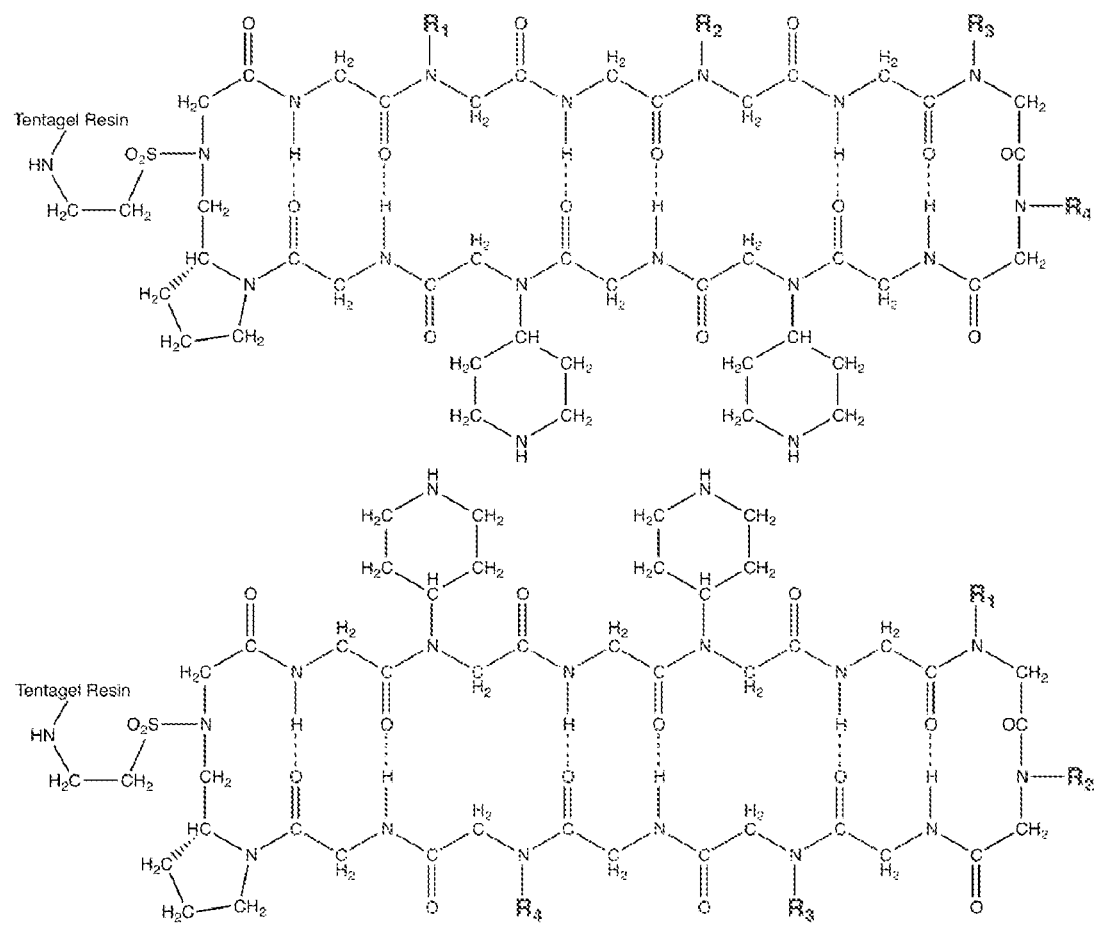
Figure 1C:
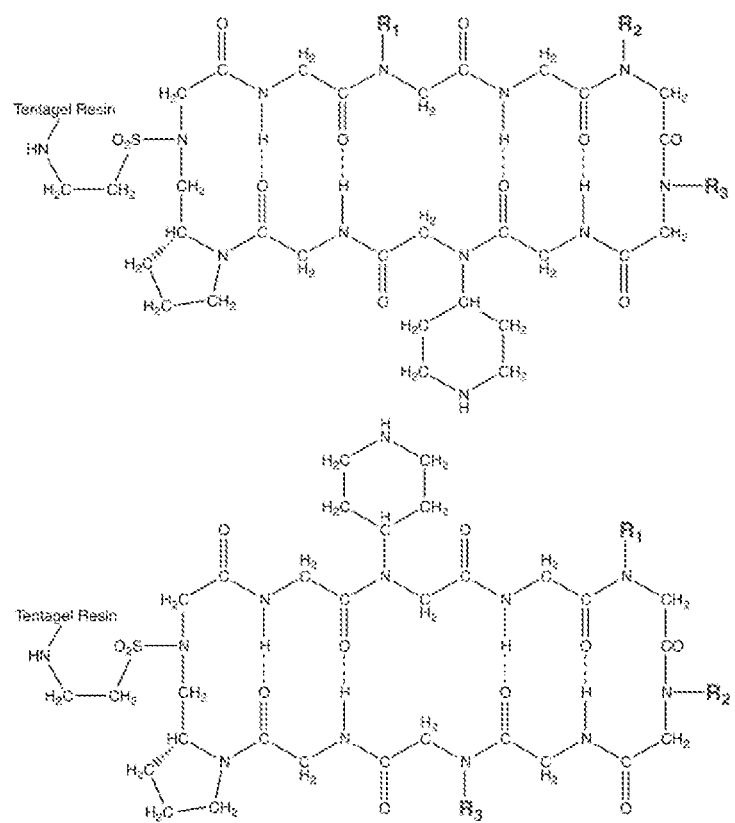
Figure 1D:
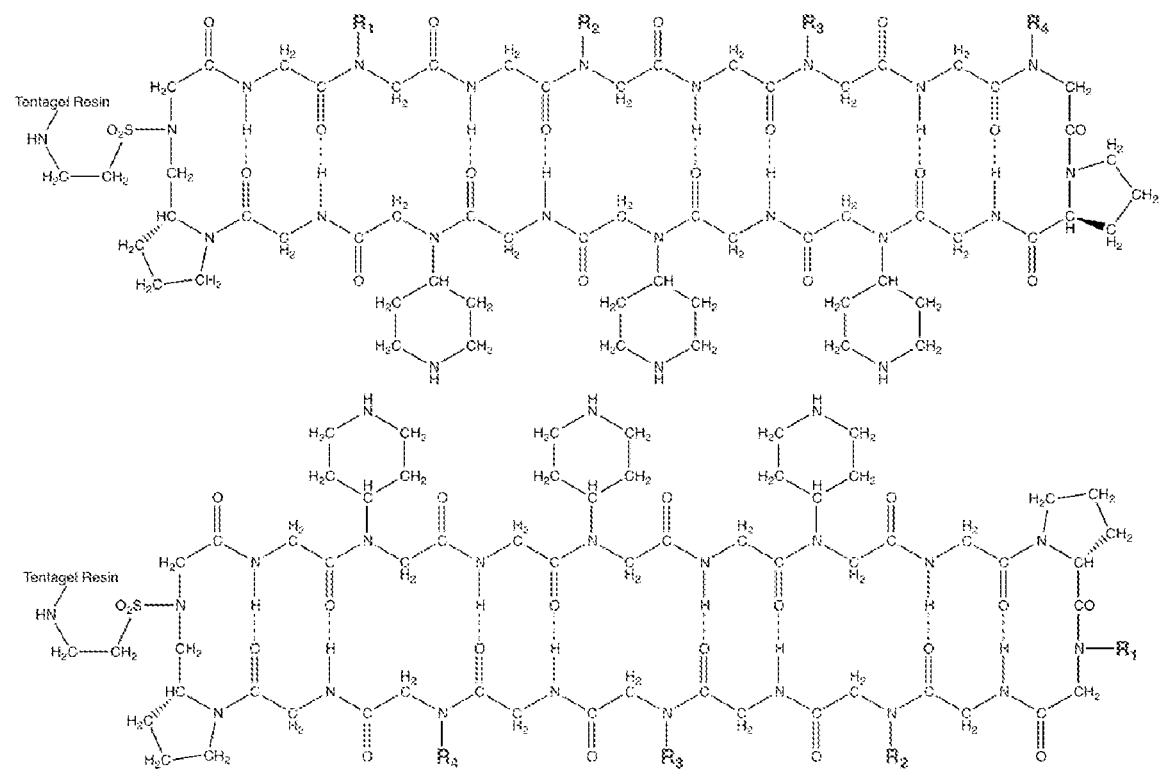

Adoptive cell transfer (ACT) is a very effective form of immunotherapy and involves the transfer of immune cells with antitumor activity into cancer patients. ACT is a treatment approach that involves the identification, in vitro, of lymphocytes with antitumor activity, the in vitro expansion of these cells to large numbers and their infusion into the cancer-bearing host. Lymphocytes used for adoptive transfer can be derived from the stroma of resected tumors (tumor infiltrating lymphocytes or TILs). They can also be derived or from blood if they are genetically engineered to express antitumor T cell receptors (TCRs) or chimeric antigen receptors (CARs), enriched with mixed lymphocyte tumor cell cultures (MLTCs), or cloned using autologous antigen presenting cells and tumor derived peptides. ACT in which the lymphocytes originate from the cancer-bearing host to be infused is termed autologous ACT. US 2011/0052530 relates to a method for performing adoptive cell therapy to promote cancer regression, primarily for treatment of patients suffering from metastatic melanoma, which is incorporated by reference in its entirety for these methods.

Disclosed are compositions and methods for ex vivo expansion of tumor-infiltrating lymphocytes (TILs) for use in ACT. In some embodiments, the methods involve culturing the lymphocytes to produce expanded lymphocytes in a culture medium comprising a toll like receptor (TLR) agonist in an amount effective to improve the tumor-specificity of the expanded lymphocytes. The TLR agonist is in some embodiments a ligand for a TLR selected from the group consisting of TLR1, TLR2, TLR3, TLR4, and TLR9. For example, the TLR agonist can be a ligand selected from the group consisting of Pam3CSK4, Pam3CSK4, poly I:C, Ribomunyl, and CpG ODN.

In other embodiments, the methods involve culturing the lymphocytes to produce expanded lymphocytes in a culture medium comprising a peptide or peptidomimetic in an amount effective to improve the tumor-specificity of the expanded lymphocytes. In some embodiments, the peptidomimetic is a peptoid or peptide-peptoid hybrid. For example, in some embodiments, the peptoid or peptide-peptoid hybrid is stabilized by a hydrocarbon staple.

The peptoid portion can provide resistant to proteolysis and the peptide portion of the peptoid-peptide hybrids can provide the ability to achieve the beta-hairpin-like secondary structure. These two contributions can result in a hybrid that is a good drug candidate for therapies where proteolysis is generally a limitation of the therapy. As disclosed herein, these peptide-peptoid hybrids can also be used for ex vivo expansion of tumor-infiltrating lymphocytes (TILs) for use in ACT.

Examples of peptide-peptoid hybrid are described in WO 2013/192628 by McLaughlin et al., which is incorporated herein by reference for the library of peptoid bodies described therein. The peptoid bodies in WO 2013/192628 are cyclic peptoid-peptide hybrids, which can provide a scaffold library using a pairwise combinatorial approach.

The cyclic peptoid-peptide hybrids can adopt a beta-hairpin-like secondary structure. This cyclic beta-hairpin-like design results from the alternation of the peptide-peptoid sub-units in two antiparallel beta-strands. For example, the disclosed peptide-peptoid hybrid can have the chemical structure, for example, shown in formula I:

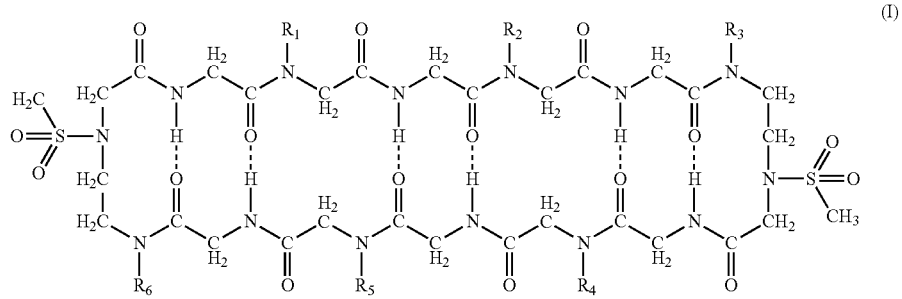

or a pharmaceutically acceptable salt or hydrate thereof, wherein $R_1$-$R_6$ are independently organic groups.

In some embodiments, the cyclic peptoid-peptide hybrids have the chemical structure shown in formula II:

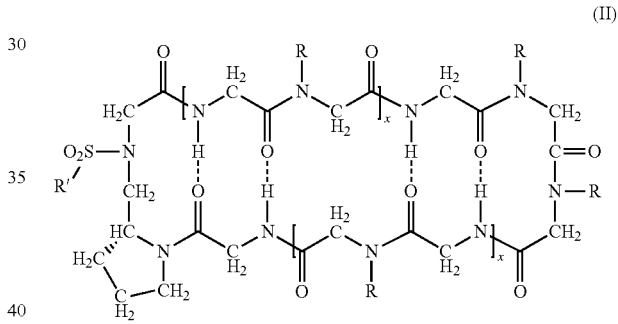

or a pharmaceutically acceptable salt or hydrate thereof, wherein R groups are independently organic groups, R' is an organic group, or an organic bridging group to a resin or other substrate, and x is 1 to 3.

In some embodiments, the cyclic peptoid-peptide hybrids have the chemical structure shown in formula III:

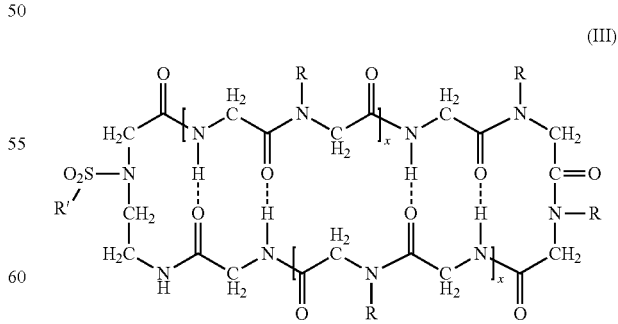

or a pharmaceutically acceptable salt or hydrate thereof, wherein R groups are independently organic groups, R' is an organic group, or an organic bridging group to a resin or other substrate, and x is 1 to 3.

In some embodiments, the cyclic peptoid-peptide hybrids have the chemical structure shown in formula IV:

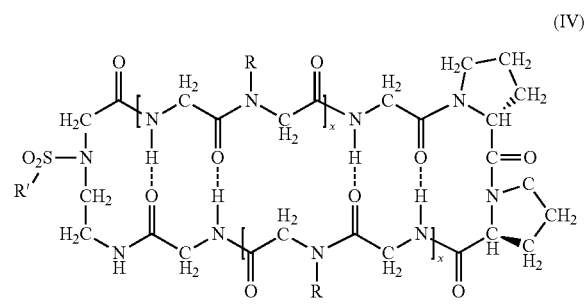

(IV)

or a pharmaceutically acceptable salt or hydrate thereof, wherein R groups are independently organic groups, R' is an organic group, or an organic bridging group to a resin or other substrate, and x is 1 to 3.

In some embodiments, the cyclic peptoid-peptide hybrids have the chemical structure shown in formula V:

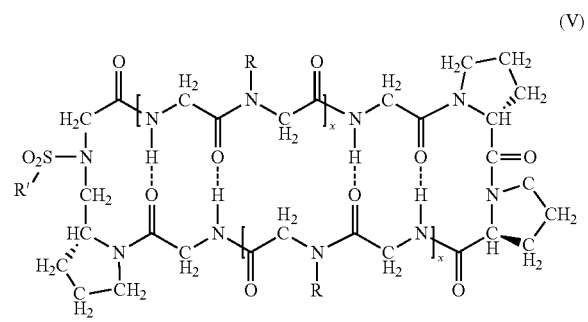

(V)

or a pharmaceutically acceptable salt or hydrate thereof, wherein, R groups are independently organic groups; R' is an organic group, or an organic bridging group to a resin or other substrate, and x is 1 to 3.

In some embodiments, the cyclic peptoid-peptide hybrids have the chemical structure shown in formula VI:

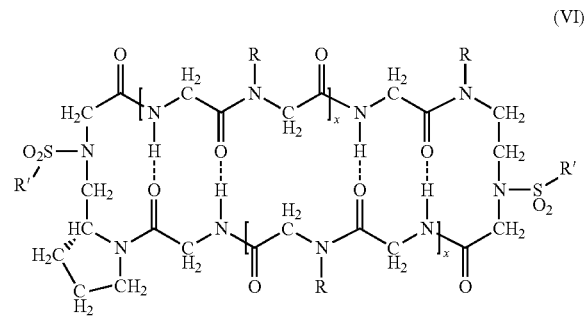

(VI)

or a pharmaceutically acceptable salt or hydrate thereof, wherein R groups are independently organic groups, R' is independently an organic group, or an organic bridging group to a resin or other substrate, and x is 1 to 3.

In some embodiments, the cyclic peptoid-peptide hybrids have the chemical structure shown in formula VII:

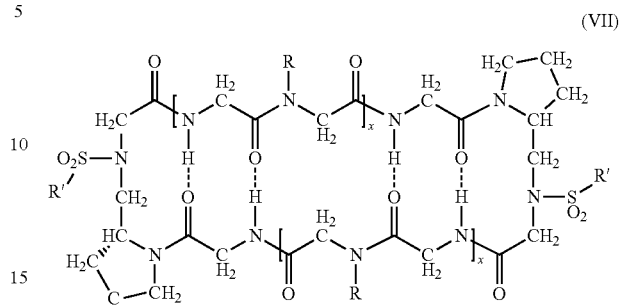

(VII)

or a pharmaceutically acceptable salt or hydrate thereof, wherein R groups are independently organic groups, R' is independently an organic group, or an organic bridging group to a resin or other substrate, and x is 1 to 3.

In some embodiments, the cyclic peptoid-peptide hybrids have the chemical structure shown in formula VIII:

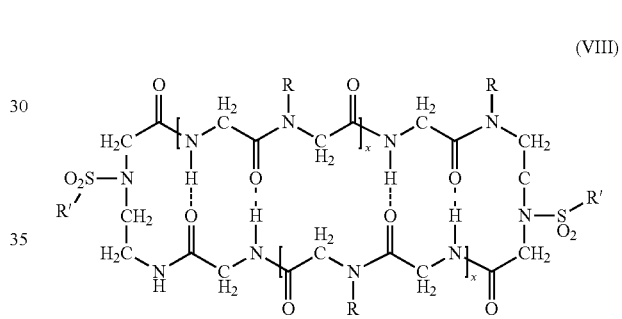

(VIII)

or a pharmaceutically acceptable salt or hydrate thereof, wherein R groups are independently organic groups, R' is independently an organic group, or an organic bridging group to a resin or other substrate, and x is 1 to 3.

In some embodiments, the cyclic peptoid-peptide hybrids have the chemical structure shown in formula IX:

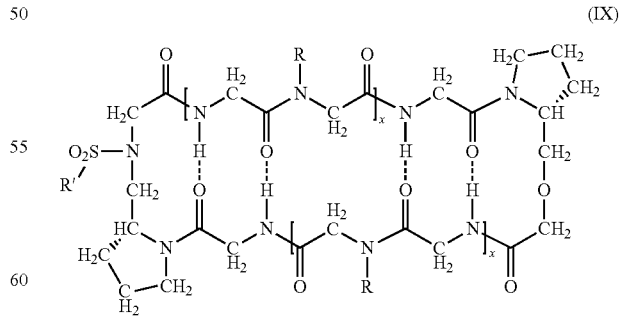

(IX)

or a pharmaceutically acceptable salt or hydrate thereof, wherein R groups are independently organic groups, R' is an organic group, or an organic bridging group to a resin or other substrate, and x is 1 to 3.

In some embodiments, the cyclic peptoid-peptide hybrids have the chemical structure shown in formula X:

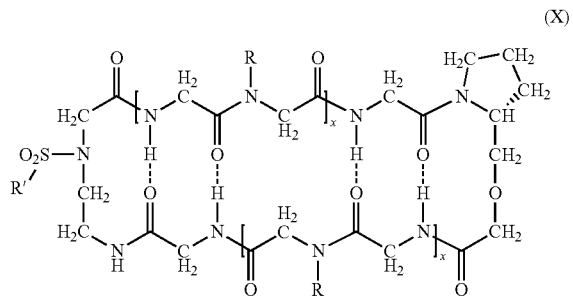

(X)

or a pharmaceutically acceptable salt or hydrate thereof, wherein R groups are independently organic groups, R' is an organic group, or an organic bridging group to a resin or other substrate, and x is 1 to 3.

In some embodiments, R groups of at least two adjacent peptoid-glycine sequences are 4-piperidinyl groups, for example, a compound of Formula II where x is 2:

fied variation thereof. The R group can be, but is not limited to, $C_1$-$C_{12}$ alkyl, $C_1$-$C_{12}$ hydroxyalkyl, $C_1$-$C_{12}$ aminoalkyl, $C_1$-$C_{12}$ carboxylic acid alkyl, $C_2$-$C_{12}$ alkyloxyalkyl, $C_2$-$C_{12}$ alkenyl, $C_2$-$C_{12}$ hydroxyalkenyl, $C_2$-$C_{12}$ aminoalkenyl, $C_1$-$C_{12}$ carboxylic acid alkenyl, $C_3$-$C_{14}$ alkyloxyalkenyl, $C_6$-$C_{14}$ aryl, $C_6$-$C_{14}$ hydroxyaryl, $C_6$-$C_{14}$ aminoaryl, $C_6$-$C_{14}$ carboxylic acid aryl, $C_7$-$C_{15}$ alkyloxyaryl, $C_4$-$C_{14}$ heteroaryl, $C_4$-$C_{14}$ hydroxyheteroaryl, $C_4$-$C_{14}$ aminoheteroaryl, $C_4$-$C_{14}$ carboxylic acid heteroaryl, $C_5$-$C_{15}$ alkoxyheteroaryl, $C_7$-$C_{15}$ alkylaryl, $C_7$-$C_{15}$ hydroxyalkylaryl, $C_7$-$C_{15}$ aminoalkylaryl, $C_7$-$C_{15}$ carboxylic acid alkylaryl, $C_8$-$C_{15}$ alkoxyalkylaryl, or a chemically transformed product of any of these R groups, such as, esters, thioesters, thiols, amides, or sulfonamides, wherein alkyl groups can be linear, branched, multiply branched, cyclic, or polycyclic. For example, R can be, a residue of a primary amine, which can be, but is not limited to, groups from the incorporation of 4-aminopiperidine, ethanolamine, allylamine, 1,4-diaminobutane, piperponylamine, 4,(2-aminoethyl)benzene, isobutylamine, tryptamine, 4-morpholinoaniline, 5-amino-2-methoxypyridine, (R)-methylbenzylamine, 1-(2-aminopropyl)-2-pyrrolidinone, furfurylamine, benzylamine, 4-chlorobenzylamine, 4-methoxybenzylamine, methoxyethylamine, 2-aminoadi-

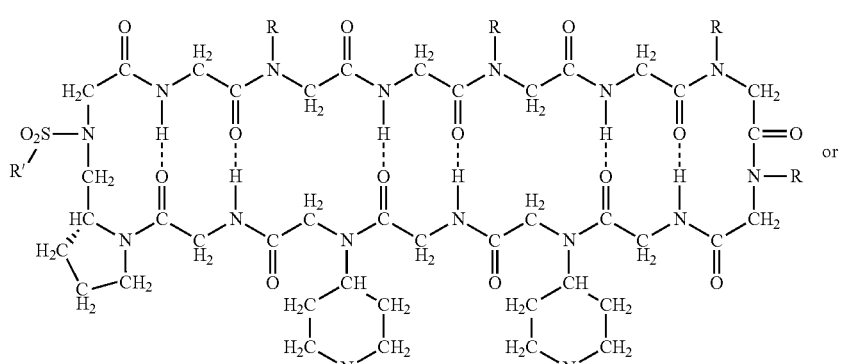

(XI)

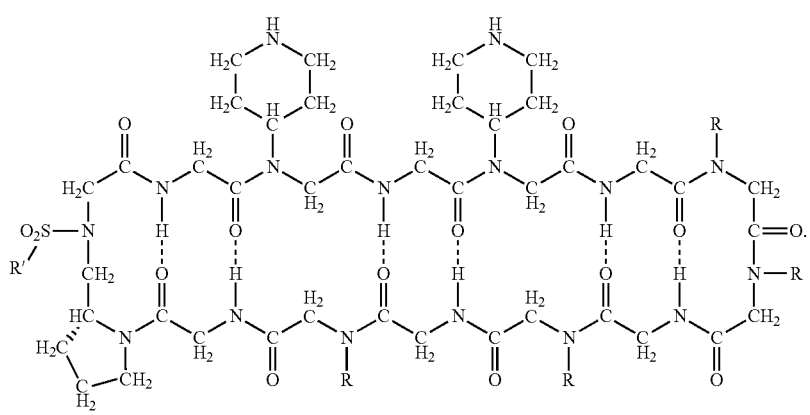

(XII)

The R groups of the cyclic peptoid-peptide hybrids of Formula I through XII above, can be of almost any structure such that it does not contain a moiety that disrupts the complementary hydrogen bonding of the beta sheet structure within the cyclic peptoid-peptide hybrid. The R group can be equivalent to the side chains of amino acids, the non-amine portion of an amino acid, or modified non-amine portion of an amino acid. The R group can be a sugar, such as, a mono-saccharide or di-saccharide, or a fatty acid, or modipic acid, N-ethylasparagine, 3-aminoadipic acid, hydroxylysine, beta-alanine, allo-hydroxylysine propionic acid, 2-aminobutyric acid, 3-hydroxyproline, 4-Aminobutyric acid, 4-hydroxyproline piperidinic acid, 6-aminocaproic acid, isodesmosine, 2-aminoheptanoic acid, allo-isoleucine, 2-aminoisobutyric acid, N-methylglycine, 3-aminoisobutyric acid, N-methylisoleucine, 2-Aminopimelic acid, 6-N-methyllysine, 2,4-diaminobutyric acid, N-methylvaline, desmosine, norvaline, 2,2'-diaminopimelic acid, norleucine, 2,3-diaminopropionic acid, ornithine, N-ethylglycine, or protected equivalents thereof, as a peptoid N-R unit in the cyclic peptoid-peptide hybrid.

Figure 2:
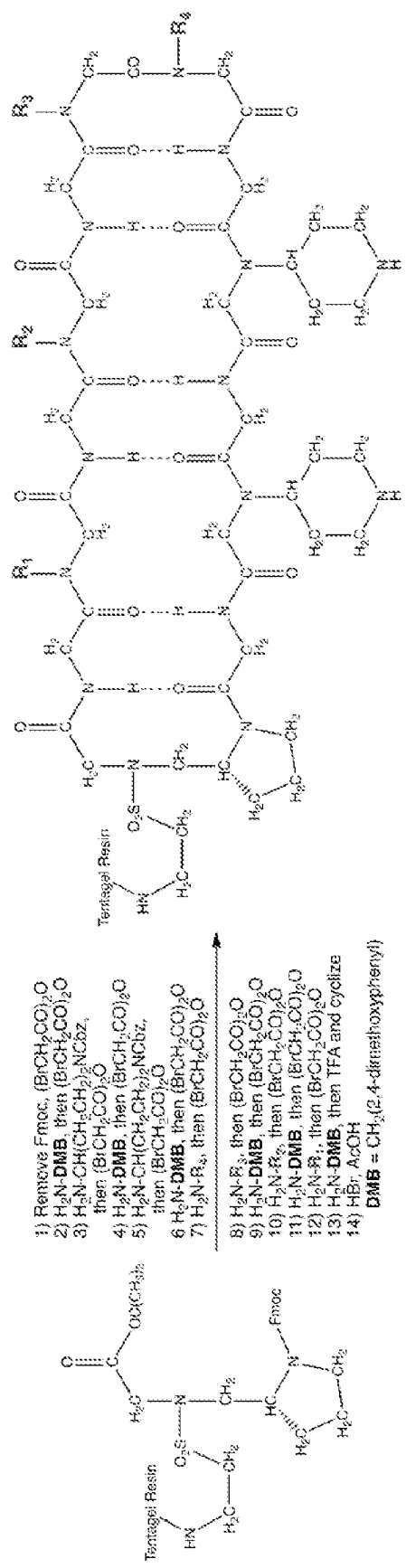
FIG. 2 shows a schematic for the preparation of a peptoid-body comprising a linker that is bound to a resin and a second linker comprising a peptoid-peptoid sequence.
Figure 3:
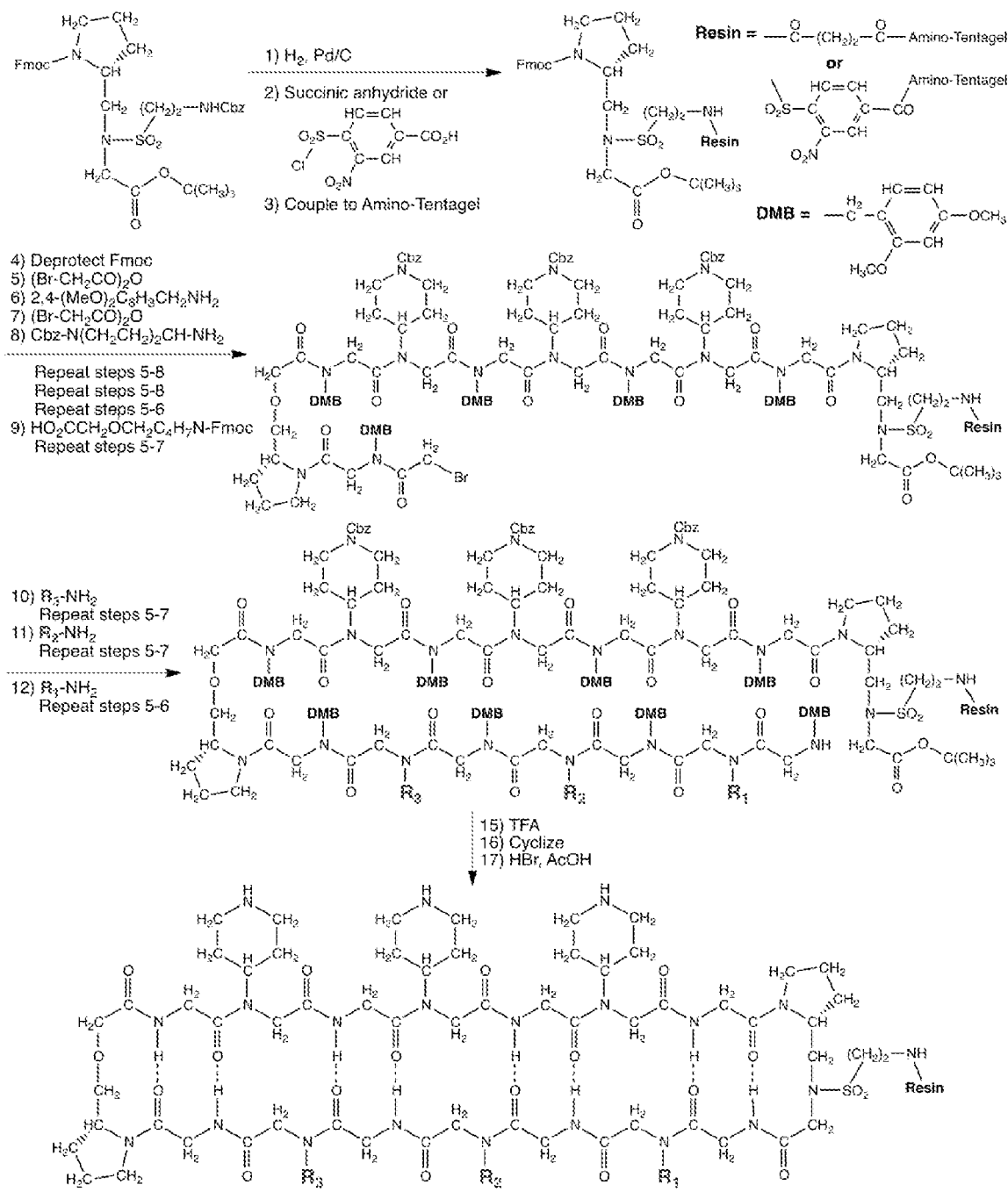
FIG. 3 shows a schematic for the preparation of a peptoid-body comprising a linker that is bound to a resin and a second linker that is a beta-turn promoter.

In some embodiments, the peptoid-peptide hybrids can be produced on a solid support, such as a resin. The hybrids can then be cleaved from the supporting resin for use in the disclosed methods. FIGS. 1 and 2 illustrate example peptoid-peptide hydrids as resin-bound intermediates.

Example Peptoid-Peptide Hybrids

Embodiment 1: A peptoid-peptide hybrid having a beta-hairpin-like conformation, comprising a plurality of alternating peptoid-peptide sequences, each having at least one peptoid residue and an amino acid residue, wherein the peptoid-peptide sequences form at least two antiparallel beta-strands between a plurality of linkers, and wherein at least one linker is a beta-turn promoter.

Embodiment 2: The hybrod according to embodiment 1, wherein at least one of the linker is the amino acid residue from the condensation of the linker precursor of the structure:

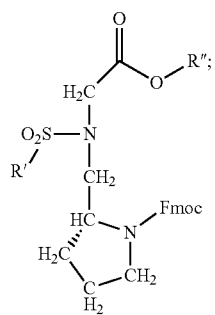

(T₁)

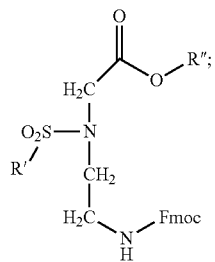

(T₂)

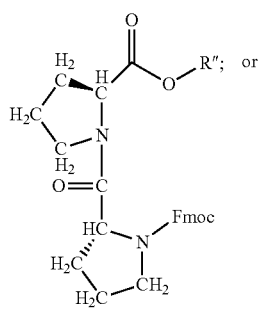

(T₃)

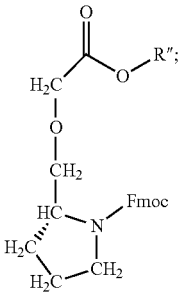

(T₄)

wherein where R' is an organic group, or an organic bridging group attached to a resin or other substrate and R" is H or a carboxylic acid protecting group.

Embodiment 3: The hybrid according to embodiment 2, wherein R" is t-butyl, allyl, or benzyl.

Embodiment 4: The hybrid according to embodiment 2, wherein the organic bridging group attached to a resin or other substrate comprises a —NH(CH₂)₂— bridging group.

Embodiment 5: The hybrid according to embodiment 1, wherein one of the linker is two peptoid residues.

Embodiment 6: The hybrid according to embodiment 1, wherein the cyclic peptoid-peptide hybrid is:

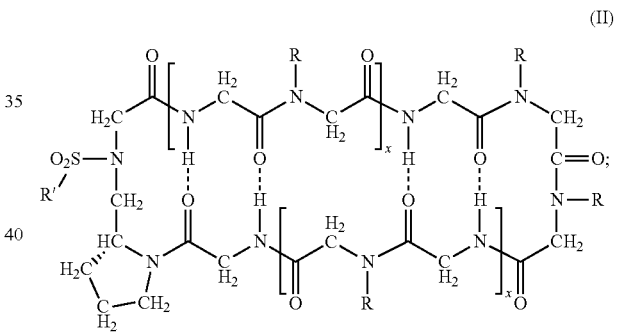

(II)

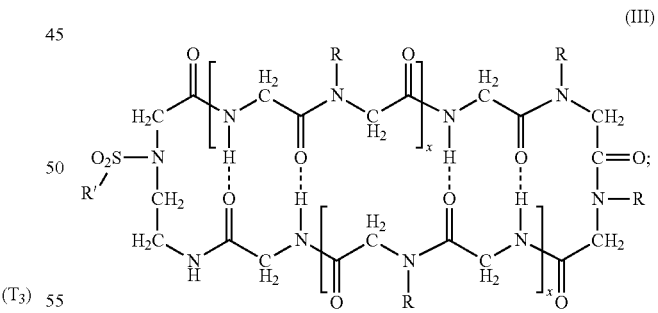

(III)

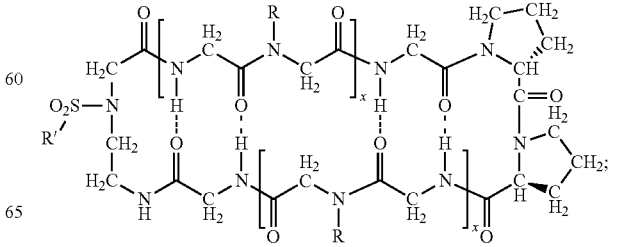

(IV)

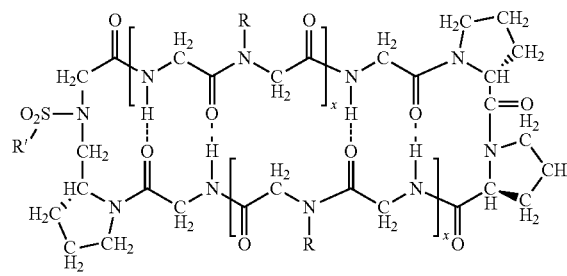

(V)

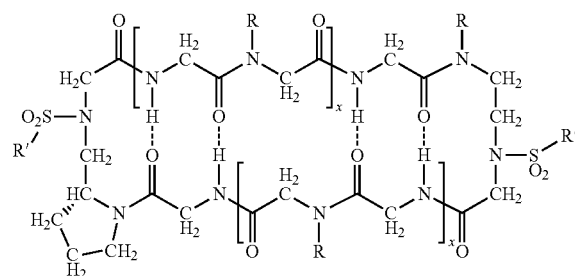

(VI)

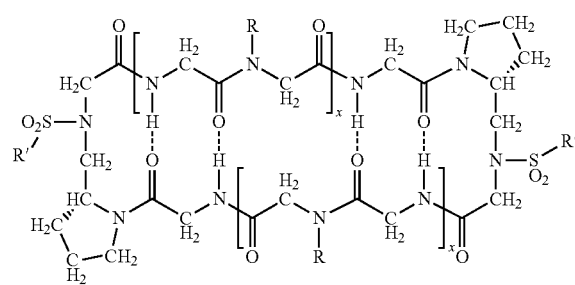

(VII)

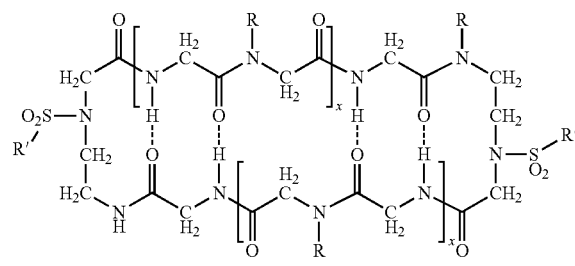

(VIII)

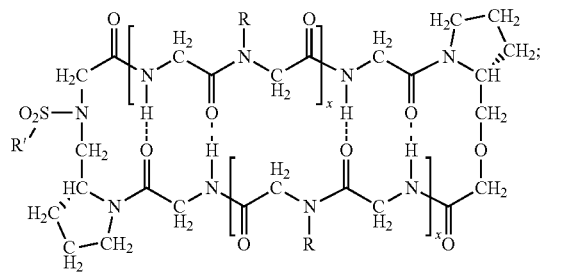

(IX)

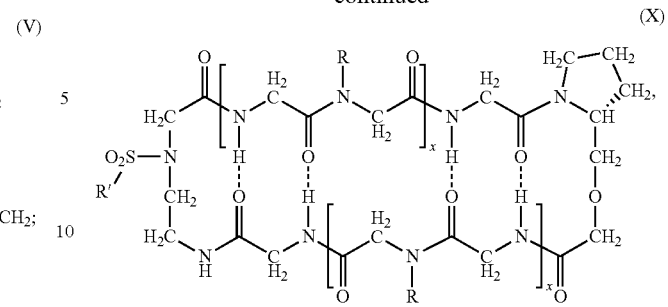

(X)

wherein R groups are independently organic groups, R' is independently an organic group or an organic bridging group attached to a resin, and x is 1 to 3.

Embodiment 7: The hybrid according to embodiment 6, wherein R is independently $C_1$-$C_{12}$ alkyl, $C_1$-$C_{12}$ hydroxyalkyl, $C_1$-$C_{12}$ aminoalkyl, $C_1$-$C_{12}$ carboxylic acid alkyl, $C_2$-$C_{12}$ alkyloxyalkyl, $C_2$-$C_{12}$ alkenyl, $C_2$-$C_{12}$ hydroxyalkenyl, $C_2$-$C_{12}$ aminoalkenyl, $C_1$-$C_{12}$ carboxylic acid alkenyl, $C_3$-$C_{14}$ alkyloxyalkenyl, $C_6$-$C_{14}$ aryl, $C_6$-$C_{14}$ hydroxyaryl, $C_6$-$C_{14}$ aminoaryl, $C_6$-$C_{14}$ carboxylic acid aryl, $C_7$-$C_{15}$ alkyloxyaryl, $C_4$-$C_{14}$ heteroaryl, $C_4$-$C_{14}$ hydroxyheteroaryl, $C_4$-$C_{14}$ aminoheteroaryl, $C_4$-$C_{14}$ carboxylic acid heteroaryl, $C_5$-$C_{15}$ alkoxyheteroaryl, $C_7$-$C_{15}$ alkylaryl, $C_7$-$C_{15}$ hydroxyalkylaryl, $C_7$-$C_{15}$ aminoalkylaryl, $C_7$-$C_{15}$ carboxylic acid alkylaryl, $C_8$-$C_{15}$ alkoxyalkylaryl, or any chemically transformed structure therefrom.

Embodiment 8: The hybrid according to embodiment 7, wherein the chemically transformed structure comprises an ester, thioester, thiol, amide, or sulfonamide.

Embodiment 9: The hybrid according to embodiment 6, wherein R is independently a residue of a primary amine: 4-aminopiperidine; ethanolamine; allylamine; 1;4-diaminobutane; piperponylamine; 4;(2-aminoethyl)benzene; isobutylamine; tryptamine; 4-morpholinoaniline; 5-amino-2-methoxypyridine; (R)-methylbenzylamine; 1-(2-aminopropyl)-2-pyrrolidinone; furfurylamine; benzylamine; 4-chlorobenzylamine; 4-methoxybenzylamine; methoxyethylamine. 2-aminoadipic acid; N-ethylasparagine; 3-aminoadipic acid; hydroxylysine; beta-alanine; allo-hydroxylysine propionic acid; 2-aminobutyric acid; 3-hydroxyproline; 4-Aminobutyric acid; 4-hydroxyproline piperidinic acid; 6-Aminocaproic acid; Isodesmosine; 2-Aminoheptanoic acid; allo-isoleucine; 2-aminoisobutyric acid; N-methylglycine; 3-aminoisobutyric acid; N-methylisoleucine; 2-Aminopimelic acid; 6-N-methyllysine; 2,4-diaminobutyric acid; N-methylvaline; desmosine; norvaline; 2,2'-diaminopimelic acid; norleucine; 2,3-diaminopropionic acid; ornithine; N-ethylglycine; or any protected equivalents thereof.

Embodiment 10: The hybrid according to embodiment 6, wherein at least one R is a residue of 4-aminopiperidine.

Embodiment 11: The hybrid according to embodiment 1, wherein all of the amino acid residues are glycine residues.

Peptoid-peptide hybrids can be further stabilized by cross linking between the amino acid side chains, and/or the N-substitutions on glycines, and/or backbone cyclization. Such peptoids are referred to herein as "stapled peptoids;" whereas, such peptoid-peptide hybrids are herein referred to as "stapled peptoid-peptide hybrids."

Stapling of peptoids or peptoid-peptide hybrids involves side chain-to-side chain linkages and/or backbone cyclization to stabilize the peptoids or the peptoid-peptide hybrids. Thus, the current invention extends the approach of stabilizing peptides using stabilized side chain linkages to stabilizing peptoids or peptoid-peptide hybrids.

For the purpose of the current invention, the term "side chain" includes a side chain on the amino acid as well as the moiety attached to the N atom of the N-substituted glycine.

Several possible side chain-to-side chain linkages (hereinafter referred to as intramolecular cross-linking) can be designed. The intramolecular cross-linking between the two sides chains of the peptoids or the peptoid-peptide hybrids of the current invention can be mediated through chemical reactions between the side chains which can also involve additional chemicals.

For example, the intramolecular cross-linking can be mediated through a chemical moiety which is not a part of the side chains and wherein the side chains connect to each other via the chemical moiety. An example of the chemical moiety forming the intramolecular cross-linking is described in FIGS. 6-9.

In some embodiments, the intramolecular cross-link is established by the RCM (ring-closing metathesis) approach according Aileron or a Click reaction (e.g., Copper Catalyzed 3+2 cycloaddition) described in U.S. Pat. No. 5,811,515, which is incorporated herein by reference in its entirety. An example of intramolecular cross-linking mediated through the RCM approach is described in FIG. 9.

In a further embodiment, the intramolecular cross-linking between the two side chains is established by formation of a chemical bond, for example, through a condensation reaction, between the functional groups present on the side chains. A condensation reaction is a chemical reaction in which two molecules or moieties (functional groups) combine via a chemical bond and the reaction involves the loss of one or more smaller molecules. Examples of condensation reaction between the side chains that can be used in producing the intramolecular cross-linking according to the current invention are well known to a person of ordinary skill in the art and such embodiments are within the purview of the current invention.

Figure 4A:
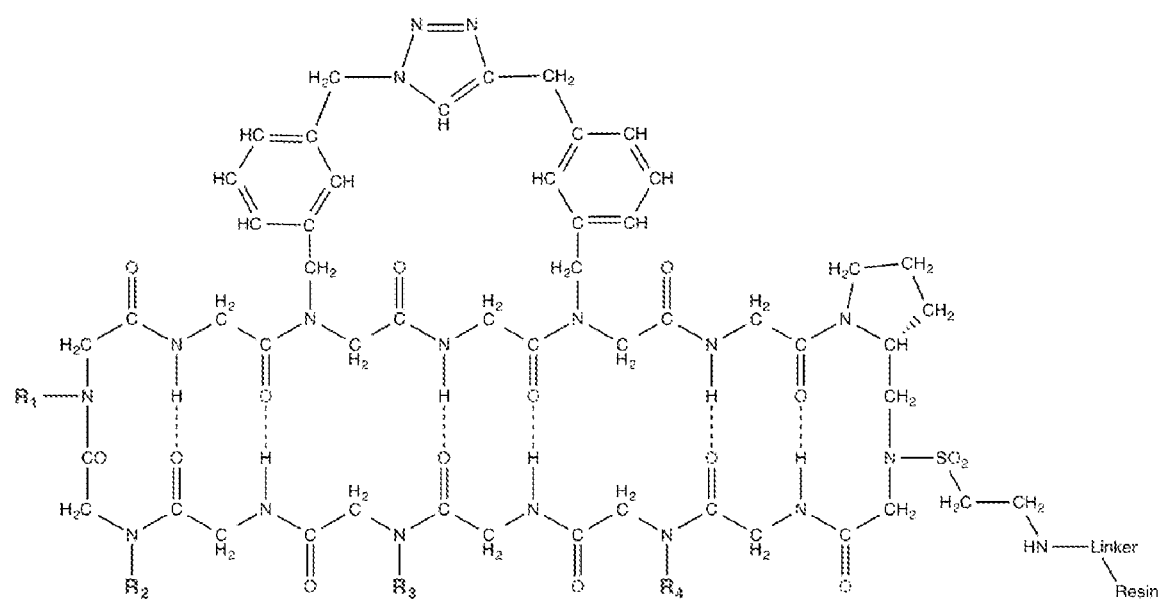
FIGS. 4A to 4C show examples of stapled peptoid-peptide hybrids.
Figure 4B:
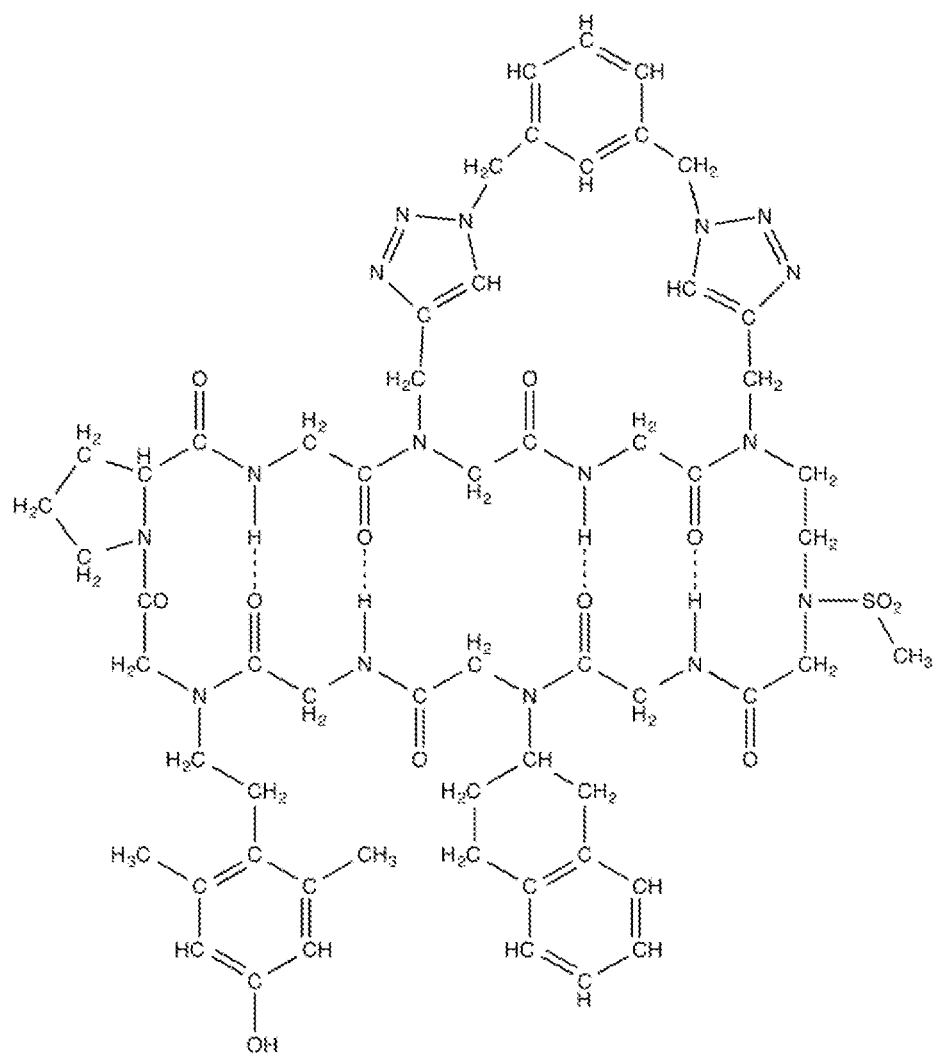
Figure 4C:
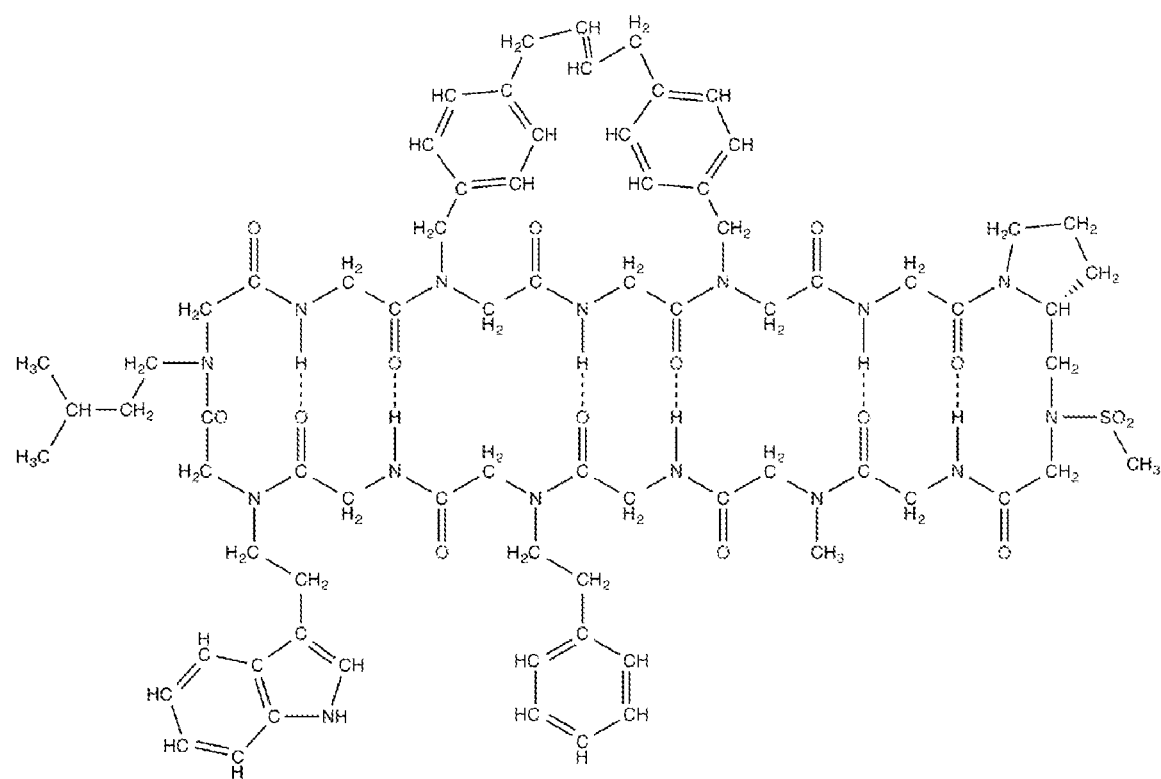

Additional examples of peptoids stapled with certain intramolecular cross-links are shown in FIGS. 4A-4C.

Additional examples of cross-links in peptides are disclosed in U.S. Pat. Nos. 8,592,377, 8,324,428, 8,198,405, 7,786,072, 7,723,469, 7,192,713, the contents of which are herein incorporated by reference in their entirety. A person of ordinary skill in the art can envision using various cross-links described in these patent documents in preparing the stapled peptoids and the stapled peptoid-peptide hybrids according to the current invention and such embodiments are within the purview of the current invention.

Accordingly, the current invention provides a stapled peptoid comprising a plurality of N-substituted glycines, wherein at least two of the N-substituted glycines are linked to each other by intramolecular cross-linking and wherein the length and geometry of the intramolecular cross-link provides stability to the peptoid.

In some cases, the stapled peptoid-peptide hybrid can comprise a plurality of amino acids and plurality of N-substituted glycines, wherein at least two residues from the plurality of amino acids and the plurality of N-substituted glycines are linked to each other by an intramolecular cross-link and wherein the length and geometry of the intramolecular cross-link provides stability to the peptoid-peptide hybrid.

In one embodiment two N-substituted glycine residues or two amino acid residues are linked to each other by a cross-link. In another embodiment, an N-substituted glycine residue is linked to an amino acid residue by a cross-link.

In a further embodiment, the stapled peptoid-peptide hybrid is a cyclic peptoid-peptide hybrid. A cyclic peptoid-peptide hybrid comprises a plurality of alternating peptoid-peptide sequences, each having at least one peptoid residue and an amino acid residue, wherein the peptoid-peptide sequences form at least two antiparallel beta-strands.

In some embodiments, the intramolecular cross-link is an all hydrocarbon cross-link.

In some embodiments, the peptoid or the peptoid-peptide hybrid comprises more than one intramolecular cross-link, for example, two, three, or four intramolecular cross-links In some embodiments, the cross-links are between two or more amino acid residues, or N-substituted glycine residues located on the same side of a beta sheet, thereby providing stability to the peptoid or peptoid-peptide hybrid. In a further embodiment, the intramolecular cross-links are between two or more amino acid residues, or N-substituted glycine residues located on the residues of a beta sheet, thereby providing stability to the peptoid or peptoid-peptide hybrid.

In some embodiments, the side chain can be selected from cyclic or acyclic, branched or unbranched, substituted cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene.

Additional examples of side chains and cross-links that can be applied in the current invention are disclosed, for example, in the U.S. Pat. No. 8,592,377 from column 37, line 26 to column 43, line 14; U.S. Pat. No. 8,198,405, column 3, line 54 to column 10, line 2 and column 25, line 14 to column 26, line 21; U.S. Pat. No. 7,786,072, column 5, line 44 to column 9, line 43 and column 11, line 16 to column 12, line 8; U.S. Pat. No. 7,723,469, column 5, line 30 to column 9, line 12 and column 24, line 60 to column 26, line 3; and U.S. Pat. No. 7,192,713, column 4, line 26 to column 9, line 45 and column 11, line 23 to column 12, line 18.

The stapled peptoids, peptoid-peptide hybrids, and stapled cyclic peptoid-peptide hybrids of the current invention can also further optionally contain substitutions in the side chains of the amino acid and/or the N-substituted glycine residues, wherein the substitutions in the side chains further stabilize the peptoids, peptoid-peptide hybrids, and cyclic peptoid-peptide hybrids. Non-limiting examples of various substitutions that could be used in the current invention are provided in Table 2.

Tumor-infiltrating lymphocyte (TIL) production is a 2-step process: 1) the pre-REP (Rapid Expansion) stage where you the grow the cells in standard lab media such as RPMI and treat the TILs w/reagents such as irradiated feeder cells, and anti-CD3 antibodies to achieve the desired effect; and 2) the REP stage where you expand the TILs in a large enough culture amount for treating the patients. The REP stage requires cGMP grade reagents and 30-40 L of culture medium. However, the pre-REP stage can utilize lab grade reagents (under the assumption that the lab grade reagents get diluted out during the REP stage), making it easier to incorporate alternative strategies for improving TIL production. Therefore, in some embodiments, the disclosed TLR agonist and/or peptide or peptidomimetics can be included in the culture medium during the pre-REP stage.

ACT may be performed by (i) obtaining autologous lymphocytes from a mammal, (ii) culturing the autologous lymphocytes to produce expanded lymphocytes, and (ii) administering the expanded lymphocytes to the mammal. Preferably, the lymphocytes are tumor-derived, i.e. they are TILs, and are isolated from the mammal to be treated, i.e. autologous transfer.

Autologous ACT as described herein may also be performed by (i) culturing autologous lymphocytes to produce expanded lymphocytes; (ii) administering nonmyeloablative lymphodepleting chemotherapy to the mammal; and (iii) after administering nonmyeloablative lymphodepleting chemotherapy, administering the expanded lymphocytes to the mammal. Autologous TILs may be obtained from the stroma of resected tumors. Tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase).

Expansion of lymphocytes, including tumor-infiltrating lymphocytes, such as T cells can be accomplished by any of a number of methods as are known in the art. For example, T cells can be rapidly expanded using non-specific T-cell receptor stimulation in the presence of feeder lymphocytes and interleukin-2 (IL-2), IL-7, IL-15, IL-21, or combinations thereof. The non-specific T-cell receptor stimulus can e.g. include around 30 ng/ml of OKT3, a mouse monoclonal anti-CD3 antibody (available from Ortho-McNeil®, Raritan, N.J. or Miltenyi Biotec, Bergisch Gladbach, Germany). Alternatively, T cells can be rapidly expanded by stimulation of peripheral blood mononuclear cells (PBMC) in vitro with one or more antigens (including antigenic portions thereof, such as epitope(s), or a cell of the cancer, which can be optionally expressed from a vector, such as an human leukocyte antigen A2 (HLA-A2) binding peptide, e.g., approximately 0.3 µM MART-1:26-35 (27 L) or gp100:209-217 (210M)), in the presence of a T-cell growth factor, such as around 200-400 Ill/ml, such as 300 IU/ml IL-2 or IL-15, with IL-2 being preferred. The in vitro-induced T-cells are rapidly expanded by re-stimulation with the same antigen(s) of the cancer pulsed onto HLA-A2-expressing antigen-presenting cells. Alternatively, the T-cells can be re-stimulated with irradiated, autologous lymphocytes or with irradiated HLA-A2+ allogeneic lymphocytes and IL-2, for example.

In some embodiments, nonmyeloablative lymphodepleting chemotherapy is administered to the mammal prior to administering to the mammal the expanded tumor-infiltrating lymphocytes. The purpose of lymphodepletion is to make room for the infused lymphocytes, in particular by eliminating regulatory T cells and other non-specific T cells which compete for homeostatic cytokines. Nonmyeloablative lymphodepleting chemotherapy can be any suitable such therapy, which can be administered by any suitable route known to a person of skill. The nonmyeloablative lymphodepleting chemotherapy can comprise, for example, the administration of cyclophosphamide and fludarabine, particularly if the cancer is melanoma, which can be metastatic. A preferred route of administering cyclophosphamide and fludarabine is intravenously. Likewise, any suitable dose of cyclophosphamide and fludarabine can be administered. Preferably, around 40-80 mg/kg, such as around 60 mg/kg of cyclophosphamide is administered for approximately two days after which around 15-35 mg/m², such as around 25 mg/m² fludarabine is administered for around five days, particularly if the cancer is melanoma.

Specific tumor reactivity of the expanded TILs can be tested by any method known in the art, e.g., by measuring cytokine release (e.g., interferon-gamma) following co-culture with tumor cells. In one embodiment, the autologous ACT method comprises enriching cultured TILs for CD8+ T cells prior to rapid expansion of the cells. Following culture of the TILs in IL-2, the T cells are depleted of CD4+ cells and enriched for CD8+ cells using, for example, a CD8 microbead separation (e.g., using a CliniMACS<plus>CD8 microbead system (Miltenyi Biotec)). In an embodiment of the method, a T-cell growth factor that promotes the growth and activation of the autologous T cells is administered to the mammal either concomitantly with the autologous T cells or subsequently to the autologous T cells. The T-cell growth factor can be any suitable growth factor that promotes the growth and activation of the autologous T-cells. Examples of suitable T-cell growth factors include interleukin (IL)-2, IL-7, IL-15, IL-12 and IL-21, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2. IL-12 is a preferred T-cell growth factor.

Preferably, expanded lymphocytes produced by these methods are administered as an intra-arterial or intravenous infusion, which preferably lasts about 30 to about 60 minutes. Other examples of routes of administration include intraperitoneal, intrathecal and intralymphatic. Likewise, any suitable dose of lymphocytes can be administered. In one embodiment, about $1 \times 10^{10}$ lymphocytes to about $15 \times 10^{10}$ lymphocytes are administered.

The cancer treated by the disclosed compositions and methods can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the vulva, chronic lymphocytic leukemia, chronic myeloid cancer, cervical cancer, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, peritoneum, omentum, and mesentery cancer, pharynx cancer, prostate cancer, rectal cancer, renal cancer, skin cancer, soft tissue cancer, testicular cancer, thyroid cancer, ureter cancer, urinary bladder cancer, and digestive tract cancer such as, e.g., esophageal cancer, gastric cancer, pancreatic cancer, stomach cancer, small intestine cancer, gastrointestinal carcinoid tumor, cancer of the oral cavity, colorectal cancer, and hepatobiliary cancer.

The cancer can be a recurrent cancer. Preferably, the cancer is a solid cancer. Preferably, the cancer is melanoma, ovarian, breast and colorectal cancer, even more preferred is melanoma, in particular metastatic melanoma.

Definitions

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The terms "peptide," "protein," and "polypeptide" are used interchangeably to refer to a natural or synthetic molecule comprising two or more amino acids linked by the carboxyl group of one amino acid to the alpha amino group of another.

As used herein, "peptidomimetic" means a mimetic of a peptide which includes some alteration of the normal peptide chemistry. Peptidomimetics typically enhance some property of the original peptide, such as increase stability, increased efficacy, enhanced delivery, increased half life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The term "peptoid" refers to a class of peptidomimetics whose side chains are appended to the nitrogen atom of the peptide backbone, rather than to the α-carbons (as they are in amino acids).

The term "tumor infiltrating lymphocyte" or "TIL" refers to white blood cells that have left the bloodstream and migrated into a tumor.

The term "regression" does not necessarily imply 100% or complete regression. Rather, there are varying degrees of regression of which one of ordinary skill in the art recognizes as having a potential benefit or therapeutic effect. The term also encompasses delaying the onset of the disease, or a symptom or condition thereof.

The term "staple" or "hydrocarbon staple" as used herein refers to the use of a hydrocarbon to stabilize the secondary structure of a synthetic peptide or peptidomimetic.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Targeting TLRs to Improve TIL Expansion and Activity

Toll-like-receptors (TLRs) are pattern recognition receptors that recognize a wide variety of microbial molecules. Binding of TLR ligands to TLRs expressed on macrophages and dendritic cells (DCs) leads to effective antigen presentation for activation of T cells and host immunity. In the tumor environment, the function of macrophages and DCs is inhibited. As disclosed herein, this suppressed state may be reversed by the administration of TLR ligands (Table 1). Exogenous TLR ligands added to TIL cultures can improve the function of DCs and macrophages resulting in increased TIL expansion and improved tumor-specific immune responses.

TABLE 1

TLR Receptors and Ligands

| Receptor | Ligand(s) | Cell types |
| --- | --- | --- |
| TLR 1 | Pam3CSK4 | monocytes/macrophages a subset of dendritic cells monocytes/macrophages |
| TLR 2 | Pam3CSK4 | Myeloid dendritic cells |
| TLR 3 | poly I:C | Dendritic cells monocytes/macrophages |
| TLR 4 | Ribomunyl | Myeloid dendritic cells monocytes/macrophages |
| TLR 9 | CpG ODN | Plasmacytoid dendritic cells |

To determine whether exogenous TLR ligands added to TIL cultures are able to increase TIL expansion and improve tumor-specificity, fresh melanoma tumors are minced into 1-2 mm$^2$ fragments in media supplement with 6000 IU/ml IL-2. Twelve fragments are cultured in IL-2 alone. Additional groups of 12 fragments are treated with the following TLR ligands: TLR1/2 ligand Pam3CSK4 (1 µg/ml), TLR3 ligand poly (I:C) (12.5 µg/ml), TLR4 ligand Ribomunyl, a clinical-grade bacteria extract (1 µg/ml), TLR9 ligand CpG ODN2006 (10 ug/ml). Culture medium is replaced with fresh medium every 2-3 days. TILs are split into new wells when they reach confluency. After 10, 20, and 30 days of culture, the total number of tumor fragments resulting in TIL growth are recorded. In addition, cells are collected from each fragment and counted. The cell numbers are compared between the IL-2 control group and TLR-ligand treated group. Individual TIL pools from each fragment are co-cultured with autologous or HLA-matched and mismatched melanoma cells for 24 hours. Culture supernatants are collected and IFN-gamma is measured by standard ELISA. The purpose of these experiments is to determine whether addition of TLR ligands results in increased growth of TIL from fragments, increased proliferation of TIL, and/or increased tumor-specific activation of TIL.

Example 2: Identification of Peptoids for TIL Proliferation and Activation

In addition to TLR agonists, other co-stimulatory molecules can be expressed by TIL. A peptoid library can be screened to identify compounds that lead to improved TIL proliferation and activation. A peptoid library containing approximately 200,000 compounds is screened in a 384-well-like format. TIL cell lines are labeled with red quantum dots and screened to identify library hits that selectively bind the red cells. Once several binding peptoids are identified, the proliferation of TILs is examined in the presence of the peptoids. Peptoids that lead to TIL proliferation (stimulatory peptoids) are further examined in a functional assay.

Using a human T cell line (AS1), the effects of stimulatory peptoids is measured on T cell function. AS1 cells are activated human CD8+ T cells that demonstrate specificity against the 624 melanoma cell line, but not the HLA-mismatched 888 melanoma cell line. AS1 cells are cultured in 6000 IU/ml IL-2 in the presence of increasing doses of stimulatory peptoids. Cells are counted on days 3, 7, 10, 14, and 21 to determine the dose of stimulatory peptoids that leads to increased proliferation of AS1 cells. To determine whether culture with stimulatory peptoids leads to enhanced T cell function, IFN-gamma, a cytokine secreted by activated T cells, is measured. AS1 cells are treated with the optimal dose of stimulatory peptoid bodies as determined above. Controls include AS1 cells alone and AS1 cells treated with anti-41BB antibody. After 7 days, AS1 cells are collected and co-cultured with 624 melanoma cells. As a negative control, AS1 cells are co-cultured with 888 melanoma cells. After 24 hours, supernatants are collected and IFN-gamma production is measured by ELISA. Comparisons are made between AS1 alone and AS1 treated with stimulatory peptoids. To further explore the efficacy of stimulatory peptoids, T cells are collected from the tumors of 10 patients with metastatic melanoma enrolled in an ongoing IRB approved clinical trials. Fragments of tumor are cultured in media containing 6000 IU/ml of IL-2 to generate pools of T cells as previously described (Pilon-Thomas S, et al. J Immunother. 2012 35(8):615-20). Irrelevant or stimulatory peptoids are added to 12 fragments per condition. Fragments treated with isotype IgG or anti-41BB antibody (10 µg/ml) are used as controls. After 21 days, T cells are collected and counted. To measure activation, T cells are co-cultured with autologous or HLA-matched tumor cells. T cells alone and T cells co-cultured with HLA-mismatched tumor cells are included as negative controls. T cells cultured in the presence of CD3/CD28 are included as a positive control. After 24 hours, supernatants are collected and IFN-gamma production is measured by ELISA. In addition, the proliferation of T cells is measured at days 7, 14 and 21 to determine whether co-culture with stimulatory peptoids leads to increased proliferation of tumor-infiltrating T cells. These studies determine whether treatment of T cells with anti-PD1 peptoid-bodies improves the proliferation and activation of anti-melanoma T cells.

Example 3: Evaluation of TIL Activity in a Murine Model

A major drawback of TIL studies is the inability to test TIL in an in vivo model. A murine model is developed to measure TIL efficacy. Using NSG mice (mice lacking B and T cells, purchased from Jackson Laboratories), primary patient melanoma tumors are implanted on the flank. When the tumor reaches 5 mm in diameter, $1 \times 10^7$ expanded TILs are transferred from matched patient samples. Tumor growth and survival are measured. Using this model, whether TIL grown in standard IL-2 media, with TLR ligands, or with stimulatory peptoids lead to better tumor rejection in vivo is examined.

Example 4: Positional Scanning with 69 Different Substituents

In some embodiments, a molecular library displaying a mixture of 69 compounds defined by the general structure in FIG. 4A having various substituents (listed in Table 2) in either the $R_1$, or $R_2$, $R_3$ positions is prepared where all of the remaining $R_1$ and $R_2$, or $R_1$ and $R_3$ or $R_2$ and $R_3$ positions display each of the possible 69×69 combinations. This equals 69×69×3, i.e. 14,283 different spots. This number is much less than having to make every possible combination of 69×69×69, i.e. 328,509 spots which would have required 952.2 plates with 345 spots per plate. The positional scanning approach only requires 41.4 plates.

In this embodiment of the positional scanning approach, only about $\frac{1}{69}^{th}$ of a pure substance is displayed per spot. When a screen finds a hit, the hit is prepared anew to verify its activity. This approach gives ~1.4% of a particular sequence represented per well and by comparing with hits from other plates that discretely display the side chains in each of the three side chains the preferred side chains can be determined.

TABLE 2

Examples of substituents at R1, R2, or R3 positions:

| | |
|---|---|
| 1 | $H_2N-CH_2-CH_2-CH_3$ |
| 2 | $H_2N-CH_2-CH_2-CH_2-CH_3$ |
| 3 | $H_2N-CH_2-CH(CH_3)_2$ |
| 4 | $H_2N-CH_2-CH_2-CH(CH_3)_2$ |
| 5 | $H_2N-CH_2$-CYCLOPENTYL |
| 6 | $H_2N-CH_2-CH_2$-CYCLOPENTYL |
| 7 | $H_2N-CH_2$-CYCLOHEXYL |
| 8 | $H_2N-CH_2-CH_2$-CYCLOHEXYL |
| 9 | $H_2N-CH_2$-PHENYL |
| 10 | $H_2N-CH_2-CH_2$-PHENYL |
| 11 | $H_2N-CH_2-CH_2-CH_2$-PHENYL |
| 12 | $H_2N-CH_2$-(1-NAPHTHYL) |
| 13 | $H_2N-CH_2-CH_2$-(1-NAPHTHYL) |
| 14 | $H_2N-CH_2-CH_2-CH_2$-(1-NAPHTHYL) |
| 15 | $H_2N-CH_2$-(2-NAPHTHYL) |
| 16 | $H_2N-CH_2-CH_2$-(2-NAPHTHYL) |
| 17 | $H_2N-CH_2-CH_2-CH_2$-(2-NAPHTHYL) |
| 18 | $H_2N-CH_2$-(4-HYDROXYPHENYL)-(TERT-BUTYL PROTECTED) |
| 19 | $H_2N-CH_2-CH_2$-(4-HYDROXYPHENYL)-(TERT-BUTYL PROTECTED) |
| 20 | $H_2N-CH_2-CH_2-CH_2$-(4-HYDROXYPHENYL)-(TERT-BUTYL PROTECTED) |
| 21 | $H_2N-CH_2$-(4-METHOXYPHENYL) |

TABLE 2-continued

Examples of substituents at R1, R2, or R3 positions:

| | |
|---|---|
| 22 | $H_2N-CH_2-CH_2$-(4-METHOXYPHENYL) |
| 23 | $H_2N-CH_2-CH_2-CH_2$-(4-METHOXYPHENYL) |
| 24 | $H_2N-CH_2$-(4-CHLOROPHENYL) |
| 25 | $H_2N-CH_2-CH_2$-(4-CHLOROPHENYL) |
| 26 | $H_2N-CH_2-CH_2-CH_2$-(4-CHLOROPHENYL) |
| 27 | $H_2N-CH_2$-(3-HYDROXYPHENYL)-(TERT-BUTYL PROTECTED) |
| 28 | $H_2N-CH_2-CH_2$-(3-HYDROXYPHENYL)-(TERT-BUTYL PROTECTED) |
| 29 | $H_2N-CH_2-CH_2-CH_2$-(3-HYDROXYPHENYL)-(TERT-BUTYL PROTECTED) |
| 30 | $H_2N-CH_2$-(3-METHOXYPHENYL) |
| 31 | $H_2N-CH_2-CH_2$-(3-METHOXYPHENYL) |
| 32 | $H_2N-CH_2-CH_2-CH_2$-(3-METHOXYPHENYL) |
| 33 | $H_2N-CH_2$-(3-CHLOROPHENYL) |
| 34 | $H_2N-CH_2-CH_2$-(3-CHLOROPHENYL) |
| 35 | $H_2N-CH_2-CH_2-CH_2$-(3-CHLOROPHENYL) |
| 36 | $H_2N-CH_2-CH_2-OCH_3$ |
| 37 | $H_2N-CH_2-CH_2-CH_2-OCH_3$ |
| 38 | $H_2N-CH_2-CH_2-OH$(TERT-BUTYL PROTECTED) |
| 39 | $H_2N-CH_2-CH_2-CH_2-OH$(TERT-BUTYL PROTECTED) |
| 40 | $H_2N-CH_2$-(3-OXETANE) |
| 41 | $H_2N-CH_2-CH_2$-(3-OXETANE) |
| 42 | $H_2N-CH_2$-4-PYRAN |
| 43 | $H_2N-CH_2-CH_2$-(4-PYRAN) |
| 44 | $H_2N-CH_2-COOH$(TERT-BUTYL PROTECTED) |
| 45 | $H_2N-CH_2-CH_2$-COOH(TERT-BUTYL PROTECTED) |
| 46 | $H_2N-CH_2$-PHENYL-4-COOH(TERT-BUTYL PROTECTED) |
| 47 | $H_2N-CH_2-CH_2$-PHENYL-4-COOH(TERT-BUTYL PROTECTED) |
| 48 | $H_2N-CH_2-CO-NHCH_3$(PROTECTED) |
| 49 | $H_2N-CH_2-CH_2-CO-NHCH_3$ |
| 50 | $H_2N-CH_2$-PHENYL-4-CO-$NHCH_3$ |
| 51 | $H_2N-CH_2-CH_2$-PHENYL-4-CO-$NHCH_3$ |
| 52 | $H_2N-CH_2-CO-N(CH_3)_2$ |
| 53 | $H_2N-CH_2-CH_2-CO-N(CH_3)_2$ |
| 54 | $H_2N-CH_2$-PHENYL-4-CO-$N(CH_3)_2$ |
| 55 | $H_2N-CH_2-CH_2$-PHENYL-4-CO-$N(CH_3)_2$ |
| 56 | $H_2N-CH_2-CH_2-NH_2$(BOC PROTECTED) |
| 57 | $H_2N-CH_2-CH_2-CH_2-NH_2$(BOC PROTECTED) |
| 58 | $H_2N-CH_2-CH_2-NH-COCH_3$ |
| 59 | $H_2N-CH_2-CH_2-CH_2-NH-COCH_3$ |
| 60 | $H_2N-CH_2$-MORPHOLINE |
| 61 | $H_2N-CH_2-CH_2$-MORPHOLINE |
| 62 | $H_2N-CH_2$-2-IMIDAZOLE(BOC PROTECTED) |
| 63 | $H_2N-CH_2-CH_2$-2-IMIDAZOLE(BOC PROTECTED) |
| 64 | $H_2N-CH_2-CH_2-CH_2$-2-IMIDAZOLE(BOC PROTECTED) |
| 65 | $H_2N-CH_2-CH_2-N=C(NH_2)_2$(BOC PROTECTED) |
| 66 | $H_2N-CH_2-CH_2-CH_2-N=C(NH_2)_2$(BOC PROTECTED) |
| 67 | $H_2N-CH_2-CH_2-CH_2-CH_2-N=C(NH_2)_2$(BOC PROTECTED) |
| 68 | $H_2N-CH_2-CH_2-CH_2-CH_2-CH_2-N=C(NH_2)_2$(BOC PROTECTED) |
| 69 | $H_2N-CH_2-CH_2$-(3-INDOLYL) |

Figure 5:
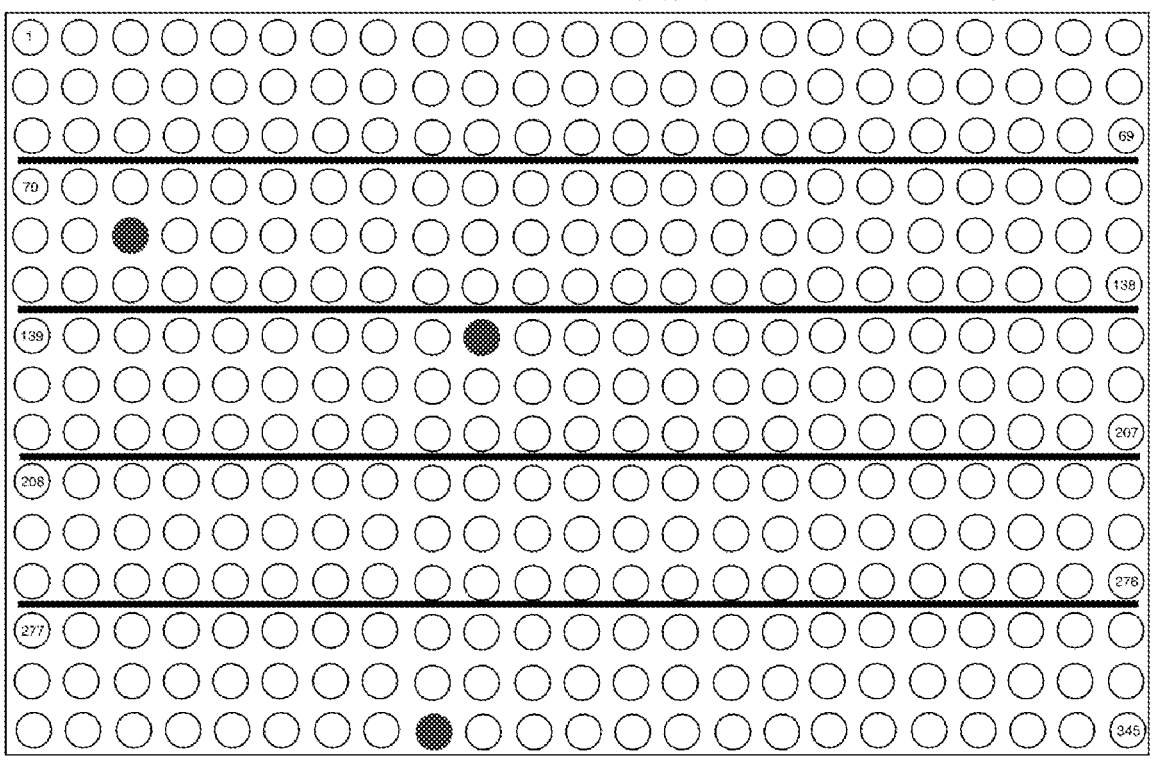
FIG. 5 shows an example of positional library scanning plate.

FIG. 5 is an example of a plate used for positional scanning Spots 1-69 would have the $R_1$ identical in all the spots and each of the individual and different 69 side chains in the $R_2$ and a mixture of all 69 compounds displayed in the $R_3$ position. Spots 70-138 would analogously have all the $R_1$ positions displaying side chain 2 and then each of the 69 different side chains in the $R_2$ position and a mixture of 69 different side chains displayed in the $R_3$ position and so on to cover all possible combinations. The specific $R_2$ plates would have a mixture of 69 compounds displayed in the $R_1$ position and then all of the 69 spots with the $R_2$ having the same side chain equal to compound 1 and then each individual 69 compounds for the $R_3$ analogous to the $R_1$ specific plates described above then the remaining combination where the $R_1$ position will display each of the 69, the $R_2$ will display the mixture of the 69 compounds, and spots 1-69 will all have the same side chain at the $R_3$ position.

An example of the results of the positional screening is also shown in FIG. 5. The first shaded spot has the best $R_1$ side chains with the side chain equal to compound 2 and $R_2$ is equal to compound 26, and at least one of the 69 possible compounds in position $R_3$. The next spot shows that compound 3 is active in $R_1$ and $R_2$ has compound 10 and at least one of the 69 compounds in position $R_3$. The last spot on the plate shows that $R_1$ equals to compound 5 and compound 55 for $R_2$ and at least one of the 69 compounds in position $R_3$. By analyzing the analogous screening results from the defined $R_2$ and $R_3$ position plates the exact sequence can be determined.

69 compounds with similar reactivity in the SN2 reaction to make the secondary amines are needed. Enormous structurally variability is possible, but some possible side chains are shown in Table 2.

Figure 6:
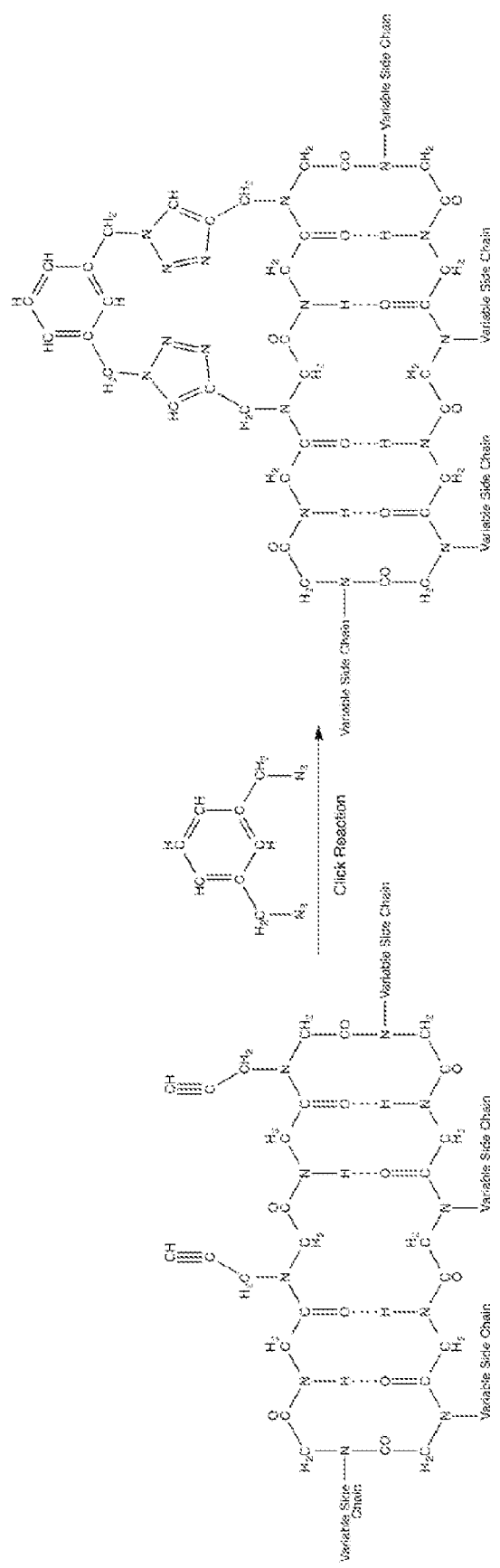
FIG. 6 shows an example of a reaction scheme to stabilize the cyclic beta-hairpin-like peptoid-peptide hybrid scaffold using a meta-xylenyl group.

Example 5: Stapling Methods to Stabilize the Cyclic Beta-Hairpin-Like Peptoid-Peptide Hybrid Scaffold There are several viable stapling methods that may be used to stabilize the cyclic beta-hairpin-like peptoid-peptide hybrid scaffold. The stapling of two peptoid side chains is the easiest to accomplish from a synthetic point of view and will pre-organize those two peptoid side chains to be proximate to each other, and that proximity enforces conformations of the overall scaffold that are compatible with the desired cyclic beta-hairpin-like secondary structure. The easiest pairs to staple are propargyl amines in the peptoid side chains to be stapled and to react those two terminal alkynes with a bifunctional diazide with a stable organic linker that spans the distance between those peptoid side chains. The organic linker needs 3 more atoms to span that distance. The meta-xylenyl group is shown in FIG. 6; however, any stable combination of atoms may be used. In addition, the chain need not be just a linker, as the group could also be used to optimize pharmacokinetics properties, for example.

Figure 7:
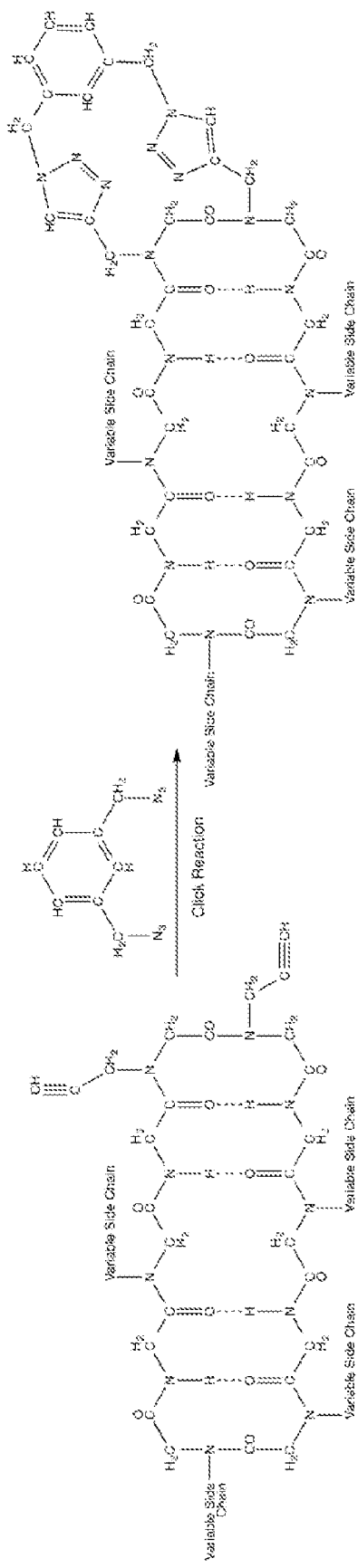
FIG. 7 shows an example of a reaction scheme to stabilize the cyclic beta-hairpin-like peptoid-peptide hybrid scaffold, by stapling propargyl side chains that are on more proximate peptide side chains.
Figure 8:
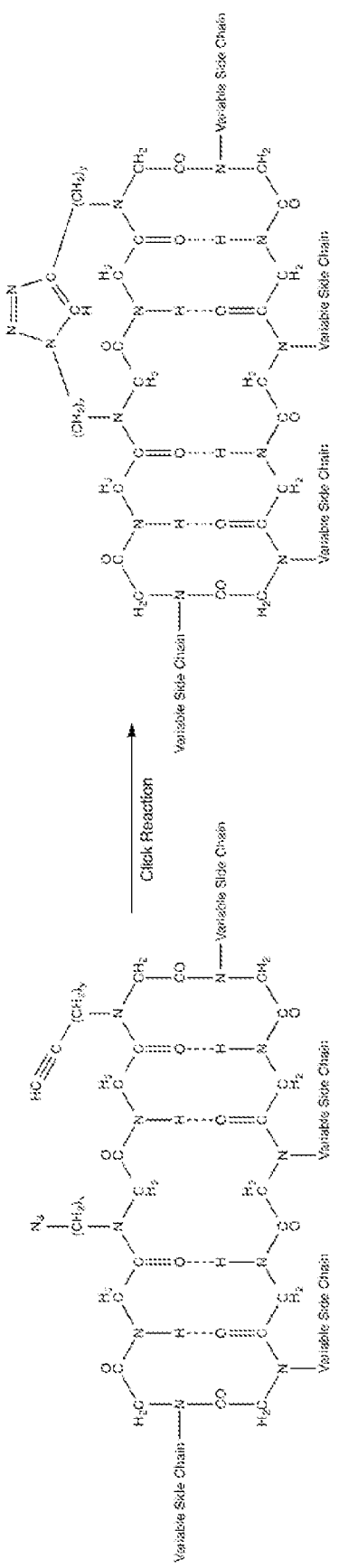
FIG. 8 shows an example of a reaction scheme to stabilize the cyclic beta-hairpin-like peptoid-peptide hybrid scaffold using an azide and an alkyne.
Figure 9:
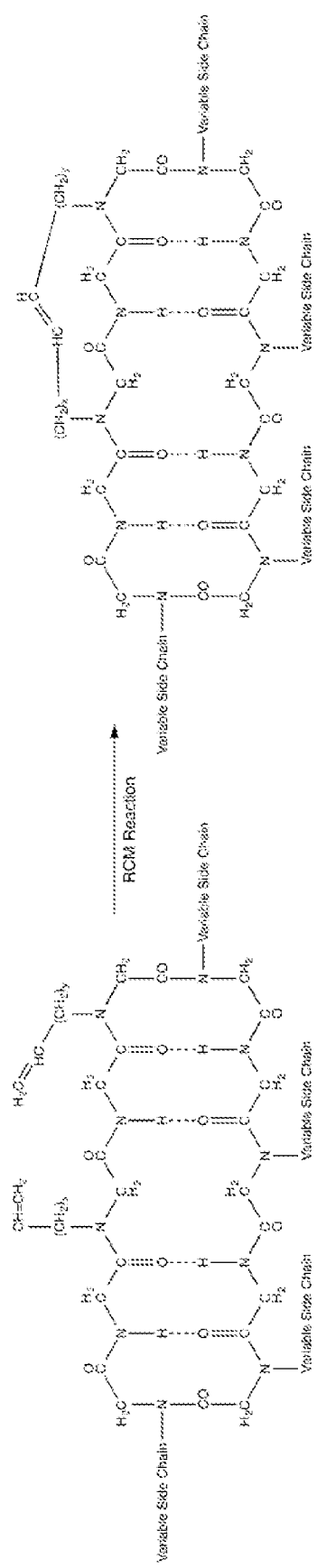
FIG. 9 shows an example of a reaction scheme to stabilize the cyclic beta-hairpin-like peptoid-peptide hybrid scaffold using ring closing metathesis (RCM).

Alternatively, the same or a different linker can be used to staple propargyl side chains that are on more proximate peptoid side chains, as shown in FIG. 7. As described herein, a side chain from an amino acid side and a proximate peptoid side chain are also possible, but not shown. A more generic scheme that uses an azide and an alkyne is shown in FIG. 8. The RCM (Ring Closing Metathesis) reaction may also be used, as shown by the generic example in FIG. 9.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of producing ex vivo expanded tumor-infiltrating lymphocytes (TILs), the method comprising:
   (a) culturing TILs from a subject in a two-step process comprising:
      (i) a pre-rapid expansion (pre-REP) stage in a first culture medium in the presence of IL-2; and
      (ii) culturing the TILs from step (i) in a rapid expansion (REP) stage in a second culture medium, comprising reagents different from reagents of the first culture medium, in the presence of IL-2 to produce expanded TILs; and
   (b) adding a toll like receptor (TLR) agonist to one or more of the first culture medium and the second culture medium in an amount effective to improve the tumor-specificity of the expanded TILs, wherein the TLR agonist is a ligand for a TLR selected from the group consisting of TLR3, and TLR9.

2. The method of claim 1, wherein the TLR agonist comprises a ligand selected from the group consisting of poly I:C, and CpG ODN.

3. The method of claim 1, wherein the subject is a human.

4. The method of claim 1, further comprising adding irradiated lymphocytes.

5. The method of claim 4, wherein the irradiated lymphocytes are autologous lymphocytes.

6. The method of claim 4, wherein the irradiated lymphocytes are irradiated allogenic lymphocytes.

7. The method of claim 6, wherein the irradiated allogenic lymphocytes are human leukocyte antigen A2 (HLA-A2) positive.

8. The method of claim 1, wherein the first culture medium comprises (i) irradiated lymphocytes, and (ii) a toll like receptor (TLR) agonist.

9. A method for producing ex vivo expanded tumor-infiltrating lymphocytes (TILs) for use in adoptive cell therapy (ACT), comprising:
   (a) culturing autologous TILs from a subject in a two-step process comprising:
      (i) a pre-rapid expansion (pre-REP) stage in a first culture medium that comprises reagents comprising IL-2; and
      (ii) culturing the TILs from step (i) in a rapid expansion (REP) stage in a second culture medium that comprises reagents comprising IL-2 to produce expanded TILs, wherein the reagents from the second culture medium are different from the reagents from the first culture medium; and
   (b) adding a toll like receptor (TLR) agonist to one or more of the first culture medium and the second culture medium in an amount effective to improve the tumor-specificity of the expanded TILs, wherein the TLR agonist is a ligand for a TLR selected from the group consisting of TLR1, TLR2, and TLR4.

10. The method of claim 9, wherein the TLR agonist comprises a ligand selected from the group consisting of Pam3CSK4, and Ribomunyl.

11. A method for treating cancer in a subject comprising the steps of:
   (a) culturing autologous tumor-infiltrating lymphocytes (TILs) from a subject in a two-step process comprising:
      (i) a pre-rapid expansion (pre-REP) stage in a first culture medium that comprises reagents comprising IL-2; and
      (ii) culturing the TILs from step (i) in a rapid expansion (REP) stage in a second culture medium that comprises reagents comprising IL-2 to produce expanded TILs, wherein the reagents from the second culture medium are different from the reagents from the first culture medium; and
   (b) adding a toll like receptor (TLR) agonist to one or more of the first culture medium and the second culture medium in an amount effective to improve the tumor-specificity of the expanded TILs, wherein the TLR agonist is a ligand for a TLR selected from the group consisting of TLR3, and TLR9;
   (c) treating the subject with nonmyeloablative lymphodepleting chemotherapy, and
   (d) administering the expanded TILs to the subject.

12. The method of claim 11, wherein the TLR agonist comprises a ligand selected from the group consisting of poly I:C, and CpG ODN.

13. The method of claim 11, wherein the cancer is a solid tumor.

14. The method of claim 11, wherein the cancer is selected from the group consisting of melanoma, ovarian cancer, breast cancer, and colorectal cancer.

15. The method of claim 11, wherein the cancer is metastatic.

16. The method of claim 11, wherein the cancer is recurrent.

17. The method of claim 11, wherein the subject is a human.

18. The method of claim 11, wherein the cancer is selected from the group consisting of acute lymphocytic cancer, acute myeloid leukemia, alveolar rhabdomyosarcoma, anal canal, bone cancer, brain cancer, breast cancer, cancer of the anorectum, cancer of the anus, cancer of the eye, cancer of the gallbladder, cancer of the intrahepatic bile duct, cancer of the joints, cancer of the middle ear, cancer of the nasal cavity, cancer of the neck, cancer of the nose, cancer of the omentum, cancer of the oral cavity, cancer of the peritoneum, cancer of the pleura, cancer of the vulva, cervical cancer, chronic lymphocytic leukemia, chronic myeloid cancer, colorectal cancer, digestive tract cancer, esophageal cancer, gastric cancer, gastrointestinal carcinoid tumor, glioma, hepatobiliary cancer, Hodgkin lymphoma, hypopharynx cancer, kidney cancer, larynx cancer, liver cancer, lung cancer, malignant mesothelioma, melanoma, mesentery cancer, multiple myeloma, nasopharynx cancer, non-Hodgkin lymphoma, ovarian cancer, pancreatic cancer, pharynx cancer, prostate cancer, rectal cancer, renal cancer, skin cancer, small intestine cancer, soft tissue cancer, stomach cancer, testicular cancer, thyroid cancer, ureter cancer, and urinary bladder cancer.

19. The method of claim 11, further comprising adding irradiated lymphocytes.

20. The method of claim 19, wherein the irradiated lymphocytes are autologous lymphocytes.

21. The method of claim 19, wherein the irradiated lymphocytes are irradiated allogenic lymphocytes.

22. The method of claim 21, wherein the irradiated allogenic lymphocytes are human leukocyte antigen A2 (HLA-A2) positive.

23. The method of claim 11, wherein the first culture medium comprises (i) irradiated lymphocytes, and (ii) a toll like receptor (TLR) agonist.

24. A method for treating cancer in a subject comprising the steps of:
    (a) culturing autologous TILs from the subject in a two-step process comprising:
        (i) a pre-rapid expansion (pre-REP) stage in a first culture medium that comprises reagents comprising IL-2; and
        (ii) culturing the TILs from step (i) in a rapid expansion (REP) stage in a second culture medium that comprises reagents comprising IL-2 to produce expanded TILs, wherein the reagents from the second culture medium are different from the reagents from the first culture medium; and
    (b) adding a toll like receptor (TLR) agonist to one or more of the first culture medium and the second culture medium in an amount effective to improve the tumor-specificity of the expanded TILs, wherein the TLR agonist is a ligand for a TLR selected from the group consisting of TLR1, TLR2, and TLR4;
    (c) treating the subject with nonmyeloablative lymphodepleting chemotherapy, and
    (d) administering the expanded TILs to the subject.

25. The method of claim 24, wherein the TLR agonist comprises a ligand selected from the group consisting of Pam3CSK4, and Ribomunyl.

* * * * *